(12) United States Patent
Cosman et al.

(10) Patent No.: US 9,919,069 B2
(45) Date of Patent: Mar. 20, 2018

(54) SYSTEMS AND METHODS FOR SANITIZING SURFACES

(71) Applicant: LivOnyx Inc., Allston, MA (US)

(72) Inventors: Maury D. Cosman, Medfield, MA (US); Bruce L. Carvalho, Watertown, MA (US)

(73) Assignee: LivOnyx Inc., Allston, MA (US)

( * ) Notice: Subject to any disclaimer, the term of this patent is extended or adjusted under 35 U.S.C. 154(b) by 0 days.

(21) Appl. No.: 15/162,114

(22) Filed: May 23, 2016

(65) Prior Publication Data

US 2016/0339132 A1 Nov. 24, 2016

Related U.S. Application Data

(60) Provisional application No. 62/197,067, filed on Jul. 26, 2015, provisional application No. 62/166,007, filed on May 24, 2015.

(51) Int. Cl.
  *A61L 2/22*  (2006.01)
  *A61L 2/26*  (2006.01)
  *A61L 2/00*  (2006.01)

(52) U.S. Cl.
  CPC .............. *A61L 2/22* (2013.01); *A61L 2/0094* (2013.01); *A61L 2/26* (2013.01); *A61L 2202/14* (2013.01); *A61L 2202/15* (2013.01)

(58) Field of Classification Search
  CPC ............. A61L 2/22; A61L 2/26; A61L 2/0094
  See application file for complete search history.

(56) References Cited

U.S. PATENT DOCUMENTS

| | | |
|---|---|---|
| 2002/0064477 A1 | 5/2002 | Vellutato |
| 2002/0151854 A1 | 10/2002 | Duchon et al. |
| 2003/0181917 A1 | 9/2003 | Gertner |
| 2004/0134494 A1 | 7/2004 | Papania et al. |
| 2004/0170526 A1 | 9/2004 | Curry et al. |
| 2004/0194207 A1* | 10/2004 | Floyd ................. E03C 1/04 4/664 |
| 2005/0281957 A1 | 12/2005 | Cooper et al. |

(Continued)

FOREIGN PATENT DOCUMENTS

WO  WO-2014165694 A2  10/2014

OTHER PUBLICATIONS

International Search Report for Application No. PCT/US2016/033792, dated Sep. 27, 2016.

*Primary Examiner* — Sean E Conley
(74) *Attorney, Agent, or Firm* — Mintz Levin Cohn Ferris Glovsky and Popeo, P.C.

(57) ABSTRACT

Systems and methods for sanitization of surfaces, such as hands, are provided. In general, the described techniques utilize a system including a housing having an active agent receptacle in fluid communication with at least one nozzle, and an air pump in fluid communication with the at least one nozzle. The system also includes a control module configured to control the delivery of an active agent as an aerosol spray through the at least one nozzle in a delivery dose. The delivery dose is expelled onto the surface as a thin uniform layer and dried such that the entire surface sanitization process is completed in less than or equal to 5 seconds. The active agent receptacle can be configured to receive a removable and replaceable cartridge carrying the active agent.

31 Claims, 27 Drawing Sheets

(56) References Cited

U.S. PATENT DOCUMENTS

Figure 1:
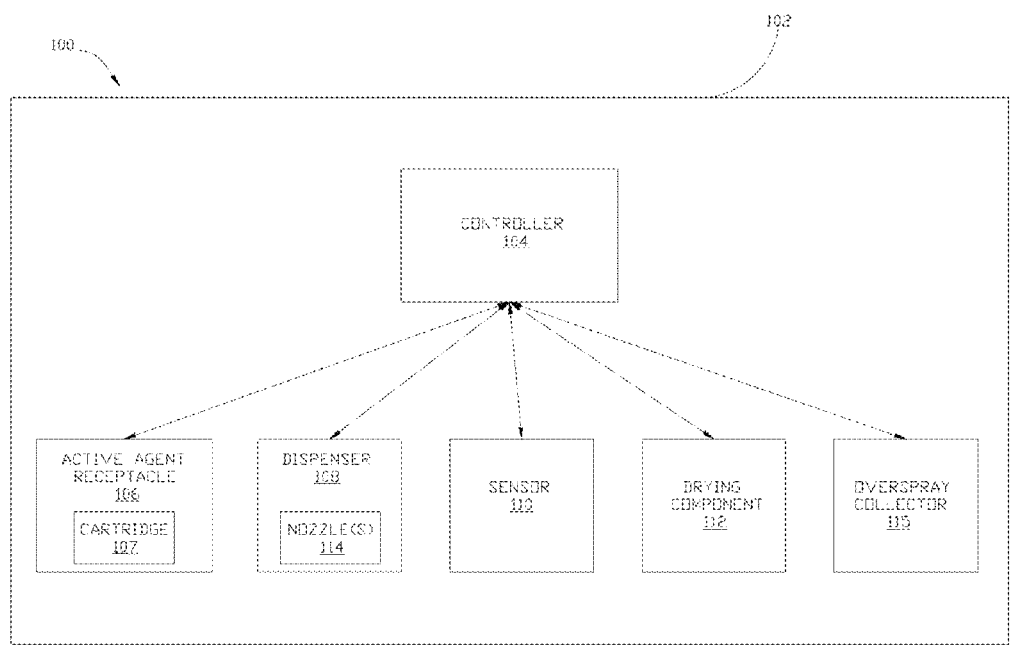

| | | |
|---|---|---|
| 2011/0223116 A1 | 9/2011 | Century |
| 2012/0288406 A1 | 11/2012 | Iwashita et al. |
| 2013/0006170 A1 | 1/2013 | Pongratz et al. |
| 2015/0000030 A1* | 1/2015 | Stine ................. A61H 35/00 4/615 |

* cited by examiner

```
700 ─╮
      ▼
   START
     │
     ▼
┌─────────────────────────────────┐
│ Detect presence of target surface│ ─── 702
└─────────────────────────────────┘
     │
     ▼
┌─────────────────────────────────┐
│    Provide airflow to nozzle    │ ─── 704
└─────────────────────────────────┘
     │
     ▼
┌─────────────────────────────────┐
│        Activate nozzle          │ ─── 706
└─────────────────────────────────┘
     │
     ▼
┌─────────────────────────────────┐
│ Provide dosage of active agent to nozzle │ ─── 708
└─────────────────────────────────┘
     │
     ▼
┌─────────────────────────────────┐
│ Dispense dosage of active agent from nozzle to surface │ ─── 710
└─────────────────────────────────┘
     │
     ▼
┌─────────────────────────────────┐
│ Activate drying component to dry active agent on surface │ ─── 712
└─────────────────────────────────┘
     │
     ▼
┌─────────────────────────────────┐
│ Provide indication of completion of drying │ ─── 714
└─────────────────────────────────┘
     │
     ▼
    END
```

FIG. 7

2505

2504

2503

2502

2501

SYSTEMS AND METHODS FOR SANITIZING SURFACES

CROSS REFERENCE TO RELATED APPLICATIONS

The present application claims priority to U.S. Provisional Patent Application No. 62/166,007, entitled "Apparatus and Method for Sanitizing Skin" filed May 24, 2015, and U.S. Provisional Patent Application No. 62/197,067, entitled "Apparatus and Method for Sanitizing Skin" filed Jul. 25, 2015, which are hereby incorporated herein by reference in their entireties.

FIELD

The present disclosure relates to systems and methods for sanitizing surfaces.

BACKGROUND

Human disease is frequently caused by pathogenic microorganisms representing the major categories of bacteria, viruses and fungi. The movement of an infectious particle from a host or infected individual to a susceptible new victim can occur by various mechanisms, including breathing of aerosolized fluids from the host, contact with surfaces contaminated by the host and host bodily fluids, or by transfer on the hands of the victim or third party from the host or from contaminated surfaces to the victim. The particular transfer mechanism depends on the organism as well as the particular setting. In hospitals and other clinical environments transfer on the hands of caregivers is considered a potentially important mechanism for organisms such as *Enterococcus faecium, Staphylococcus aureus, Klebsiella pneumoniae, Acinetobacter baumannii, Pseudomonas aeruginosa*, and *Enterobacter* species (collectively known as ESKAPE pathogens) and *Clostridium difficile*. Additionally, multi-drug resistant organisms (MDROs), defined as microorganisms, predominantly bacteria, that are resistant to one or more classes of antimicrobial agents, have special clinical significance because of their acquired resistance. MDROs include but are not limited to Methicillin Resistant *S. aureus* (MRSA), Carbapenem Resistant Enterobacteriaceae (CRE), Multidrug-resistant *A. baumannii* (MDR-Ab), and Vancomycin-Resistant *Enterococcus* (VRE). The number of viable organisms and the site of contact required to start an infection in a new host depend on the infectivity of the organisms as well as the immune capacity of the new prospective host. Individuals with compromised or weak immune function, such as hospital patients, are typically more likely to become hosts for new infections. Hospital-acquired infections have become a significant problem for the health-care industry. The severity of this problem is likely to continue to increase as additional pathogenic organisms with antibiotic resistance arise.

Some microorganisms, such as norovirus, an intestinal pathogen, are a significant concern in the cruise ship industry and in assisted care/nursing home environments, where propagation can be rapid within a close-knit community. The illnesses caused can be life-threatening. The food preparation industry, for example, large-scale poultry packaging facilities, are periodically linked to outbreaks of antibiotic-resistant *Salmonella enterica*, causing numerous deaths. The role of hand contact in the spreading and transmission of the norovirus and salmonella organisms in these settings is likely to be significant.

The importance of good hand hygiene in clinical and food-preparation environments is well established, typically promoted in terms of hand washing or use of topical alcohol-containing gels. The conventional approaches, however, have certain limitations. Hand washing can remove contaminating superficial organisms without causing significant harm to the indigenous organisms found in the skin of healthy individuals. To be effective, hand-washing should take on the order of 30 seconds. However, this amount of time is prohibitive in fast-paced, high-stress critical care settings, and does not allow additional time for hand drying. Availability of sinks can also limit the use of this approach. Although the dispensing, application, and drying of an alcohol gel on the hands can be accomplished significantly faster than hand washing and drying, these steps also require a relatively long time—approximately 10-15 seconds.

Accordingly, there is a need for improved techniques and devices for sanitizing surfaces and hands in health care, home, and other settings.

SUMMARY

In some aspects, a system for killing or inactivating a pathogen is provided that can include a housing having an active agent receptacle in fluid communication with at least one nozzle, an air pump in fluid communication with the at least one nozzle; and a control module configured to control the delivery of an active agent as an aerosol through the at least one nozzle in a delivery dose. The system is configured to deliver the delivery dose to a target surface as a thin, uniform, dried coating in a time period that is less than or equal to 5 seconds. The surface can be any suitable surface. For example, it can be a surface of one or both hands.

The system can vary in any number of ways. For example, the system can further include an air tank configured to provide air to the at least one nozzle. The system can also include a pressure regulator configured to control pressure at the at least one nozzle. As another example, the system can further include a display communicatively coupled to the control module and configured to display information related to operation of the system. The display can be any suitable display and, in some embodiments, can be an interactive display configured to receive instructions related to operation of the system.

The system can include at least one sensor configured to detect presence of the target surface in proximity to the at least one nozzle. The at least one sensor can be an optical motion sensor or any other sensor.

In some embodiments, the system includes a drying component configured to dry the delivery dose delivered to the target surface. In some embodiments, the system can include a pressure-based fluid pump.

In some embodiments, the active agent receptacle houses a removable and refillable reagent-containing cartridge. In other embodiments, the active agent receptacle is configured as a reservoir that receives a supply of the active agent.

The active agent can include any one or more ingredients. For example, it can be selected from the group consisting of an aqueous solution of hydrogen peroxide, an aqueous solution of hypochlorous acid, an aqueous solution of isopropyl alcohol, an aqueous solution of ethanol, an aqueous solution of peracetic acid, an aqueous solution of acetic acid, an aqueous solution of sodium hypochlorite, an aqueous solution of ozone, and any combination thereof. In some embodiments, the active agent can include an aqueous mixture of peracetic acid and hydrogen peroxide.

The active agent can have any suitable concentration of one or more ingredients. For example, in some embodiments, the aqueous solution of hydrogen peroxide can have from about 0.3% to about 15% of hydrogen peroxide. In other embodiments, the aqueous solution of hydrogen peroxide can have about 0.33%, 1%, 3%, 6%, 9%, or 12% of hydrogen peroxide.

The aqueous solution of hypochlorous acid can have about 0.046% of hypochlorous acid. The aqueous solution of isopropyl alcohol can have at least about 70% of isopropyl alcohol.

The at least one nozzle can vary in many different ways. For example, the at least one nozzle can be a single stationary nozzle. In other embodiments, the at least one nozzle can be two or more stationary nozzles, or two or more moveable nozzles. In some embodiments, the at least one nozzle can be an ultrasonic nozzle. In other embodiments, the at least one nozzle can be an airflow-based atomizing nozzle.

In some embodiments, the system can include at least one actuator configured to receive user input to activate the at least one nozzles. The at least one nozzle can be configured to deliver a uniform layer of the active agent to the target surface, the uniform layer having a thickness from about 1 µm to about 50 µm. In some embodiments, the uniform layer has a thickness from about 5 µm to about 20 µm.

In some aspects, a method for killing or inactivating pathogens on a surface is provided. The method can include spraying an aerosolized layer of an active agent onto the surface, the layer being a thin and substantially uniform coating. The spraying can occur over a first time period and the aerosolized layer is effective to dry over a second time period while being effective to kill or inactivate the pathogen on the surface, and wherein a duration of the first and second time periods is less than 5 seconds.

The method can vary in many different ways. For example, the pathogens can include bacteria, viruses, fungi, spores thereof or any combination thereof. The bacteria can include *Enterococcus faecium, Staphylococcus aureus, Klebsiella pneumoniae, Acinetobacter, Pseudomonas aeruginosa*, and *Enterobacter* ("ESKAPE"). As another example, the bacteria can include at least one of *Escherichia coli, Salmonella enterica*, and *Listeria monocytogenes*. The viruses can be nonenveloped viruses, which can include norovirus, rhinovirus, coxsackievirus, rotavirus or any combination thereof. The viruses can also include enveloped virus, which can include influenza virus. The spore can include spores of *Clostridium difficile*.

The duration of the first and second time periods can vary. For example, the duration of the first and second time periods can be less than 3 seconds. In some cases, the first time period is about 1 second or less. In some cases, the second time period is about 2 seconds or less.

The layer of the active agent can be from about 1 µm to about 50 µm in thickness.

In one aspect, the described techniques provide a method including, when a hand or hands placed adjacent to a nozzle is detected, delivering a thin, uniform layer of pathogen inactivation fluid or germicidal fluid onto the surfaces of the hand or hands, followed by allowing the fluid to dry. This process is completed within a short time, preferably less than 5 seconds.

In another aspect, the described techniques provide a low-volume (and consequently a low-dose) yet efficacious application of pathogen inactivation or germicidal fluid to the skin. The low-dose of an active agent provides minimal irritation or toxicity to the skin. The use of the low-dose of the active agent expands a set of safe, non-irritating and non-toxic fluids beyond antiseptic fluids to include disinfectant fluids that are normally used for inactivating or killing pathogens on inanimate surfaces.

In another aspect, a method is provided that includes providing the delivered layer of pathogen inactivation fluid or germicidal fluid that is thin enough to dry adequately via evaporation in less than 5 seconds.

In another aspect, a method is provided where drying of the pathogen inactivation fluid or germicidal fluid is assisted by drawing of air across the hands or by exposure of the hands to infrared radiation.

In another aspect, control of the drying process and the time over which the hands are wet is used to control the duration over which pathogen inactivation fluid or germicidal fluid is efficacious.

In another aspect, control of the drying process and the time over which the hands are wet is used to minimize potential skin irritation and toxicity effects of the pathogen inactivation fluid or germicidal fluid by stopping its activity via drying of the fluid.

In another aspect, control of the drying process and the time over which the hands are wet is used to minimize harm to the resident microflora on the skin.

In one aspect, the described method is efficacious at inactivating or killing a variety of types of pathogens, including bacteria, fungi, viruses or spores. In another aspect, this method includes selectively inactivating or killing pathogens on the surface of the hands while not substantially inactivating or killing the resident microflora of the hands.

In another aspect, the described techniques are efficacious at inactivating or killing a variety of strains of bacterial pathogens such as, for example, the ESKAPE pathogens, *Escherichia coli, Salmonella enterica*, and *Listeria monocytogenes*.

In some aspects, the described techniques are efficacious at inactivating or killing nonenveloped viruses such as norovirus, rhinovirus, coxsackievirus and rotavirus. In other aspects, the described techniques are efficacious at inactivating or killing enveloped viruses such as influenza virus. In yet other aspects, the described techniques are efficacious at inactivating or killing spores of *Clostridium difficile*.

In some aspects, the active agent includes a pathogen inactivation fluid or germicidal fluid that is an aqueous solution of hydrogen peroxide.

In one embodiment, the pathogen inactivation fluid or germicidal fluid is an aqueous solution of hypochlorous acid.

In another embodiment, the pathogen inactivation fluid or germicidal fluid is an aqueous solution of isopropyl alcohol.

In another embodiment, the pathogen inactivation fluid or germicidal fluid is an aqueous solution of ethanol.

In another embodiment, the pathogen inactivation fluid or germicidal fluid is an aqueous solution of peracetic acid.

In another embodiment, the pathogen inactivation fluid or germicidal fluid is an aqueous solution of acetic acid.

In another embodiment, the pathogen inactivation fluid or germicidal fluid is an aqueous solution of sodium hypochlorite.

In another embodiment, the pathogen inactivation fluid or germicidal fluid is an aqueous solution of ozone (or ozonated water).

In another embodiment, the pathogen inactivation fluid or germicidal fluid is a mixture of ozonated water and aqueous hydrogen peroxide.

In another embodiment, the pathogen inactivation fluid or germicidal fluid is an aqueous mixture of peracetic acid and hydrogen peroxide.

In some aspects, an airflow-based atomizing spray system is provided that can deliver a thin, uniform layer of an active agent including a pathogen inactivation fluid or germicidal fluid to a hand surface.

In other aspects, a pressure-based atomizing spray system is provided that can deliver a thin, uniform layer of pathogen inactivation fluid or germicidal fluid to a hand surface.

In other aspects, an ultrasonic spray system is provided that can deliver a thin, uniform layer of pathogen inactivation fluid or germicidal fluid to a hand surface.

Figure 23:
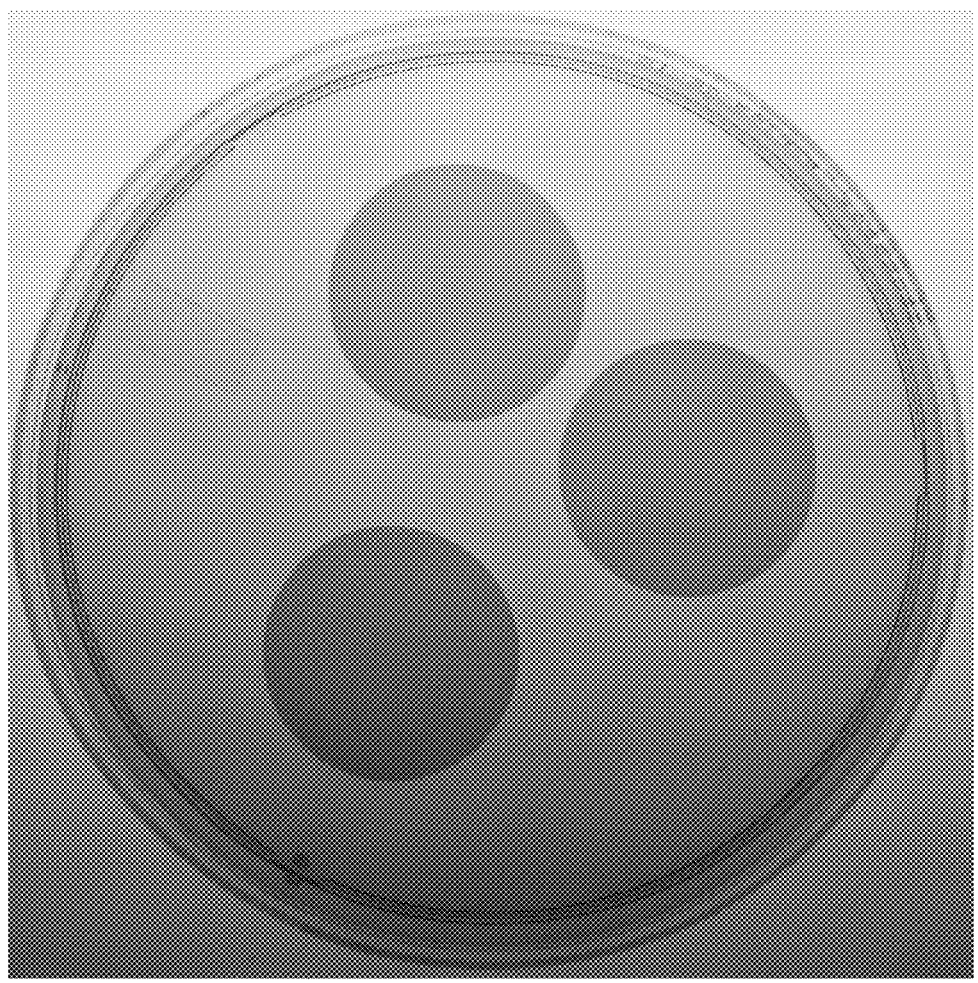
Figure 24:
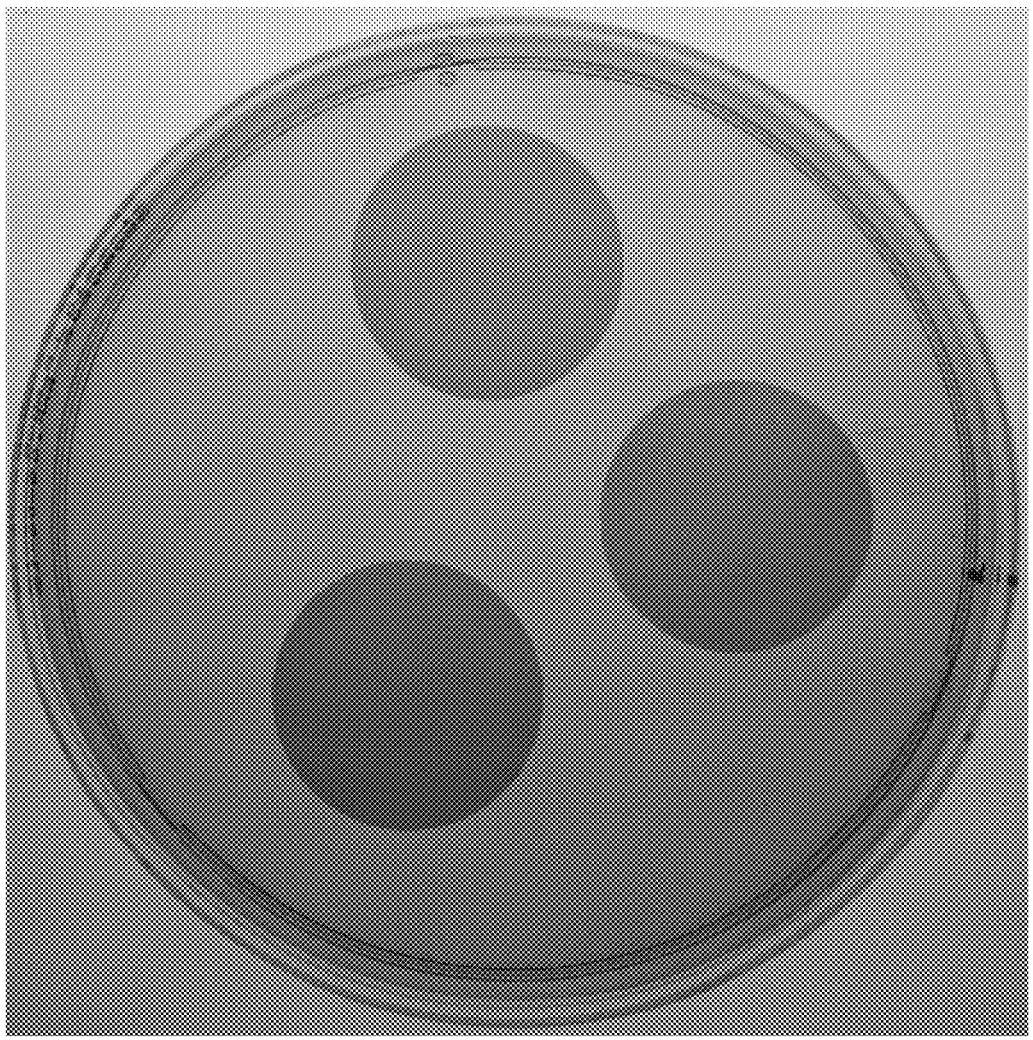

In some embodiments, the described system incorporates a blower to push or pull air across the hands in order to speed up the drying of pathogen inactivation fluid or germicidal fluid.

In some embodiments, the described system incorporates a combination heater and blower to push heated air across the hands in order to speed up the drying of pathogen inactivation fluid or germicidal fluid.

In some embodiments, the described system delivers infrared heat to the hands in order to hasten the drying of pathogen inactivation fluid or germicidal fluid.

In some embodiments, an air-atomizing spray system is provided that can deliver a layer of coating of pathogen inactivation fluid or germicidal fluid having a thickness from about 4 μm to about 10 μm to a hand surface. The coating, which can be dried within 5 seconds, is efficacious against one or more strains of *Escherichia coli.*

It should be appreciated that while the techniques provided herein are described as being used to sanitize one or both hands as a target surface, the techniques can be applied to any other target surface, including any inanimate surface.

BRIEF DESCRIPTION OF THE DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings:

FIG. 1 is a schematic diagram of a system in which the described techniques can be implemented;

FIG. 2A is another schematic diagram of a system in which the described techniques can be implemented;

FIG. 2B is another schematic diagram of a system in which the described techniques can be implemented;

FIG. 2C is another schematic diagram of a system in which the described techniques can be implemented;

FIG. 3 is a schematic illustration of a system having a stationary nozzle that can dispense an active agent to a surface such as a hand;

FIG. 4 is a schematic illustration of a system having an array of nozzles that can dispense an active agent to a surface such as a pair of hands;

FIGS. 5A-5C are schematic illustrations of a moveable array of nozzles that can be used with a sanitization system to dispense an active agent to a surface such as a pair of hands;

FIG. 6 is a flowchart of a method of sanitizing a surface in accordance with the described techniques;

FIG. 7 is a flowchart of a method of sanitizing a surface in accordance with the described techniques;

FIG. 8 is an image of an agar plate showing results of an experiment demonstrating the efficacy of an application of an active agent onto fingers coated with bacteria;

FIG. 9 is another image of an agar plate showing results of another experiment demonstrating the efficacy of an application of an active agent onto fingers coated with bacteria;

FIG. 10 is an image of an agar plate showing results of an experiment demonstrating substantial bacterial growth on membranes exposed to a 10,000-fold diluted bacterial solution;

FIG. 11 is another image of an agar plate showing results of another experiment demonstrating substantial bacterial growth on membranes exposed to a 10,000-fold diluted bacterial solution;

FIG. 12 is an image of an agar plate showing results of another experiment demonstrating moderate bacterial growth on membranes exposed to a 100,000-fold diluted bacterial solution;

FIG. 13 is an image of an agar plate showing results of another experiment demonstrating limited bacterial growth on membranes exposed to a 1,000,000-fold diluted bacterial solution;

FIG. 14 is an image of an agar plate showing results of an experiment demonstrating no bacterial growth on membranes exposed to a 10,000-fold diluted bacterial solution when a 3% aqueous solution of hydrogen peroxide was used to treat the membranes;

FIG. 15 is an image of an agar plate showing results of an experiment demonstrating no bacterial growth on membranes exposed to a 100,000-fold diluted bacterial solution when a 3% aqueous solution of hydrogen peroxide was used to treat the membranes;

FIG. 16 is an image of an agar plate showing results of an experiment demonstrating no bacterial growth on membranes exposed to a 1,000,000-fold diluted bacterial solution when a 3% aqueous solution of hydrogen peroxide was used to treat the membranes;

FIG. 17 is an image of an agar plate showing results of an experiment demonstrating no bacterial growth on membranes exposed to a 10,000-fold diluted bacterial solution when a 1% aqueous solution of hydrogen peroxide was used to treat the membranes;

FIG. 18 is an image of an agar plate showing results of an experiment demonstrating limited bacterial growth on membranes exposed to a 10,000-fold diluted bacterial solution when a 0.33% aqueous solution of hydrogen peroxide was used to treat the membranes;

FIG. 19 is an image of an agar plate showing results of an experiment demonstrating no bacterial growth on membranes exposed to a 10,000-fold diluted bacterial solution when a dilute aqueous solution of hypochlorous acid was used to treat the membranes;

FIG. 20 is an image of an agar plate showing results of an experiment demonstrating limited bacterial growth on membranes exposed to a 100,000-fold diluted bacterial solution when a dilute aqueous solution of hypochlorous acid was used to treat the membranes;

FIG. 21 is an image of an agar plate showing results of an experiment demonstrating no bacterial growth on membranes exposed to a 1,000,000-fold diluted bacterial solution when a dilute aqueous solution of hypochlorous acid was used to treat the membranes;

FIG. 22 is an image of an agar plate showing results of an experiment demonstrating no bacterial growth on membranes exposed to a 10,000-fold diluted bacterial solution when a 70% aqueous solution of isopropyl alcohol was used to treat the membranes;

FIG. 23 is an image of an agar plate showing results of an experiment demonstrating no bacterial growth on membranes exposed to a 100,000-fold diluted bacterial solution when a 70% aqueous solution of isopropyl alcohol was used to treat the membranes;

FIG. 24 is an image of an agar plate showing results of an experiment demonstrating no bacterial growth on membranes exposed to a 1,000,000-fold diluted bacterial solution when a 70% aqueous solution of isopropyl alcohol was used to treat the membranes; and FIGS. 25A-25E show images of membranes, where each membrane is pre-deposited with approximately 30,000 *Bacillus subtilis* spores and treated with (A) aqueous hydrogen peroxide solution having 12% hydrogen peroxide concentrations, (B) aqueous hydrogen peroxide solution having 9% hydrogen peroxide concentrations, (C) aqueous hydrogen peroxide solution having 6% hydrogen peroxide concentrations, (D) aqueous hydrogen peroxide solution having 3% hydrogen peroxide concentrations, and (E) distilled water.

DETAILED DESCRIPTION

Certain exemplary embodiments will now be described to provide an overall understanding of the principles of the systems and methods disclosed herein. One or more examples of these embodiments are illustrated in the accompanying drawings. Those skilled in the art will understand that the systems and methods specifically described herein and illustrated in the accompanying drawings are non-limiting exemplary embodiments and that the scope of the embodiments is defined solely by the claims. Further, the features illustrated or described in connection with one exemplary embodiment may be combined with the features of other embodiments. Such modifications and variations are intended to be included within the scope of the described embodiments.

The embodiments described herein generally relate to systems and methods for sanitizing surfaces, including body surfaces such as, for example, hands, in various environments. The described techniques involve delivering a uniform, thin layer of an active agent to a target surface being treated in a manner that allows inactivating or killing superficial, or transient, microorganisms. The active agent is delivered to a target surface quickly and in a controlled manner, and it rapidly dries on the treated surface as well. Specifically, in some examples, the agent is delivered onto the surface in less than one or two seconds or less than a half-a-second, and it can be dried on the surface within a few seconds or less than a second. For example, in some embodiments, the entire sanitizing process involving delivery of an active agent to a target surface and drying the active agent can take less than ten seconds. In other embodiments, the sanitizing process can take less than five seconds. In yet other embodiments, the sanitizing process can take less than three seconds. Thus, the target surface can be reliably sanitized in a matter of seconds.

The active agent, as used herein, is a single ingredient or a mixture of two or more ingredients such as antiseptic or disinfectant agents that inactivate or kill a variety of types of transient pathogens, including bacteria, fungi, viruses or spores. In some aspects, the active agent that can be applied to sanitize hands selectively inactivates or kills the transient pathogens on the hands' surface while not substantially affecting viability of resident microflora of the hands.

The systems and methods described herein have a number of advantages. In particular, as mentioned above, the process of covering a target surface with an active agent can be completed in less than ten, or even less than three to five seconds. Such an improved timing of the process of sanitizing the surface, and, more particularly, hand sanitizing can be especially advantageous in a healthcare or other setting where timely and frequent hand sanitizing is essential. Further, the active agent can be delivered to a surface being treated as a low dose without compromising the efficacy of the agent's sanitizing action. This can be particularly beneficial when the active agent is delivered to hands. Specifically, the low dose provides less irritation or toxicity to the skin and thus allows repeated application of the agent to maintain the proper sanitary condition of person's hands. For example, a health worker can sanitize his/her hands multiple times during the day without inconvenience or becoming uncomfortable. This can also improve compliance of health professionals with hand sanitizing standards, which can substantially reduce hospital infections and thus save lives. In addition, because of the way in which active agents can be delivered using the described techniques, in some settings, harsher active agents can be used than those that would typically be used to avoid excessive skin irritation. At the same time, as mentioned above, the described sanitizing process can be gentler on the natural (resident) microflora of the hand.

The described techniques can be used in conjunction with a variety of surfaces, including inanimate surfaces and surfaces of human body parts, such as, for example, hands (either with or without gloves), and in a variety of different environments.

The system that can implement the described surface sanitization techniques can have various components and it can atomize the active agent using a number of different approaches. Regardless of its specific configuration, and type and number of components, the system operates to deposit an active agent onto a target surface in a form of an aerosol spray. A variety of technologies can be used in the system to produce the aerosol spray.

Before describing examples of the techniques presented herein, non-limiting definitions of certain terms as used herein are provided. Thus, the term "resident microflora" refers to the community of resident microorganisms that are considered to be permanent inhabitants of the skin. These resident microorganisms are found on or within the epidermal layer of the skin.

The term "pathogens" refers to bacteria, fungi, viruses or spores that are capable of causing disease. The term "transient pathogens" refers to pathogens found on the outer layer of the skin, where they do not normally reside. Transient pathogens are typically deposited on the skin through direct contact with a contaminated surface.

FIG. 1 shows generally one embodiment of a system 100 for sanitizing surfaces in which the described techniques can be implemented. The system 100 has a housing 102 including a controller 104, an active agent receptacle 106, an active agent dispenser 108, a sensor 110, a drying component 112, and an optional overspray collector 115. It should be appreciated that the housing 102 can include other components that are not shown in FIG. 1 for the sake of simplicity. Thus, the system 100 includes one or more aerosolizing, or atomizing, components configured to transform an active agent present in the active agent dispenser 108 into an aerosol. The system can be an airflow-based atomizing spray system, a pressure-based atomizing spray system, an ultrasound spray system, or other type of an atomizing system. Also, not all communicative connections that exist between the components shown in FIG. 1 and other components are shown in FIG. 1.

The system 100 can be stationary—for example, it can be configured to be attached to a wall or other surface. In some cases, the system 100 can be moveable. Also, the system 100 can be part of another system that includes other components. As an example, the system 100 can be part of a moveable cart that can have, in addition to the system 100, a glove storage compartment, a supply of an active agent, and any other features related to sanitizing hands.

In this example, the system 100 includes the sensor 110 that can be associated with the housing 102 in various ways and that can be used to determine that the system 100 should be activated to sanitize a target surface. In some embodiments, the sensor 110 can be a proximity sensor that detects that the target surface is in proximity to the active agent dispenser 108. It should be appreciated, however, that the sensor 110 is shown by way of example only. Thus, in some embodiments, other trigger mechanism can be used additionally or alternatively to activate the system 100 to perform a target surface sanitization process. For example, the system 100 can be associated with a footswitch, one or more buttons, or one or more other suitable mechanism(s) that can receive a command (e.g., user input) to initiate the system 100. Furthermore, the system 100 can be configured such that it can be activated in response to a voice command, an instruction received via a touch-screen display or a sensor, or in any other way.

The target surface can be any suitable surface. In the examples illustrated herein, the target surface is one hand or both hands of a person. The hand(s) can be gloved or the target surface can be the skin surface. It should be appreciated that any other surface can be sanitized using the system 100. The target surface can be brought in proximity to the active agent dispenser 108. For example, one or both hands can be placed into a suitable location in proximity to the active agent dispenser 108. Furthermore, in implementations in which the system 100 or a similar system in accordance with the described techniques is portable, the system 100 can be brought to a location of the surface being sanitized.

The active agent receptacle 106 can be configured as a reservoir that can receive and store the active agent. The active agent can be created in situ and delivered to the reservoir. In some embodiments, the active agent receptacle 106 can house a removable and refillable reagent-containing cartridge 107. However, in some cases, the cartridge can be disposable and not refillable. The cartridge 107 can be configured to removably fit into the active agent receptacle 106 such that the active agent from the cartridge 107 can be accessed by the system and provided to the nozzles as required.

The dispenser component 108 includes one or more spray nozzles 114 configured to dispense the active agent in the form of an aerosol once the surface to be treated is detected by the sensor 110 or when the system 200 is activated in any other suitable way. The nozzles 114 can be disposed so as to deliver the active agent in a desired manner onto a target surface. Operation of the dispenser 108 is controlled by the controller 104. The spray nozzles 114 can be stationary or moveable, as discussed in more detail below. Regardless of their specific arrangement, configuration, and number, the spray nozzles 114 are controlled by the controller 104 to deliver a certain amount of the active agent as an aerosol dosage.

The drying component 112 of the housing 102 can be activated by the controller 104 in response to detection of the target surface in proximity to the housing 102. The drying component 112 can have a variety of different configurations. For example, it can be configured as a blower/dryer that can provide an airstream directed such that the target surface sprayed by the active agent dispensed from the nozzles 114 is dried by the airstream. The drying component 112 can have any other suitable configuration.

The overspray collector 115 can have a number of different configurations. Regardless of its specific configuration and shape, the overspray collector 115 within the housing is configured to collect any excess spray. Following a sanitizing cycle, airflow can be directed across the surface of the overspray collector 115 to cause evaporation. In some embodiments, additionally or alternatively, excess amount of spray may be collected to a drain or other receptacle for removal from the apparatus and disposal.

Systems 200, 200', 200" in FIG. 2A, FIG. 2B, and FIG. 2C, respectively, illustrate more detailed examples of the system 100 shown in FIG. 1. As shown in FIG. 2A, the system 100 includes a housing 202 which can be similar to the housing 102 of FIG. 1. As shown, the housing 202 includes, among other components, an air tank 204, an air pump 214, an active agent receptacle 206, a fluid pump 228, a nozzle component 208 having one or more nozzles, a sensor module 210 having one or more sensors configured to detect a target surface in proximity to the nozzle component 208, an optional drying component 238, an optional overspray collector 240, and a controller 212 operatively coupled to a display 213. In this example, the target surface is shown in the form of a hand 207 being sprayed with an active agent 209, though it should be appreciated that any other surface can be sanitized using the system 200. The air tank 204 and the active agent receptacle 206 are used to deliver air and an active agent, respectively, to the nozzle component 208 such that the active agent is delivered to a target surface as an aerosol that is deposited onto the surface as a thin layer. The aerosol can be generated in many suitable ways. The system 200 can be an airflow-based atomizing spray system, an ultrasound spray system, or other type of an atomizing system (e.g., a pressure-based atomizing spray system, etc.).

In the described system, the air pump 214, the air tank 204, the active agent receptacle 206, the nozzle module 208, as well as other components of the housing 202, are controlled via the controller 212. The display 213 is communicatively coupled to the controller 212 and is configured to display information related to operation of the system in any suitable form. The display 213 can be an interactive display configured to receive instructions related to operation of the system. The controller 212 can be implemented in hardware, software, or combination thereof.

The air tank 204 has a pressure sensor 205 associated therewith that is configured to monitor pressure in the tank 204. As shown in FIG. 2A, the air tank 204 is coupled to the air pump 214 that is controlled to draw ambient air and deliver it to the air tank 204. A communication line between the air pump 214 and the air tank 204 can be equipped with a pressure gauge 211 as shown in FIG. 2A. The air drawn by the air pump 214 can be passed via an air filter 216. The air is provided from an outlet 218 of the air tank 204 to the nozzle component 208 via a conduit 220. As shown, the air can be passed through a filter 222 and its delivery to the nozzle component 208 is controlled via a control valve 224. A pressure regulator component 226 controls pressure of the air passed through the conduit 220. Operation of the air pump 214 maintains pressure in the air tank 204, under control by the controller 212.

The active agent receptacle 206 is in fluid communication with the fluid pump 228 that delivers a dosage of the active agent from the receptacle 206 to the nozzle component 208. The controller 212 controls the volume and delivery time of a dose. The dosage can be preset such that one or more nozzles of the nozzle component 208 deliver a predetermined amount of the active agent each time the nozzles are activated. In some embodiments, however, the dosage can be determined by the controller 212 dynamically, based on size and other properties of a target object to be sanitized. The properties of the object can be determined using the sensor component 210 or in other ways. For example, the display 213 or other component of the system can be interactive, and can be used to receive user input regarding the surface being sanitized, including an input to activate the system 200. For example, in some embodiments, two or more options can be provided such that the user can select (e.g., by pressing a button or hovering a hand over the button) whether one hand, both hands, or any other surface can be sanitized. Furthermore, similar to system 100 in FIG. 1, the system 200 can receive instructions via a suitable mechanism such as a button, touchscreen, footswitch, or other control mechanism configured to activate the system. The control mechanism can be coupled to the housing 102 (e.g., it can be attached to the housing or coupled thereto via a wired connection) or it can be a remote device wirelessly communicating with components of the housing.

Figure 2A:
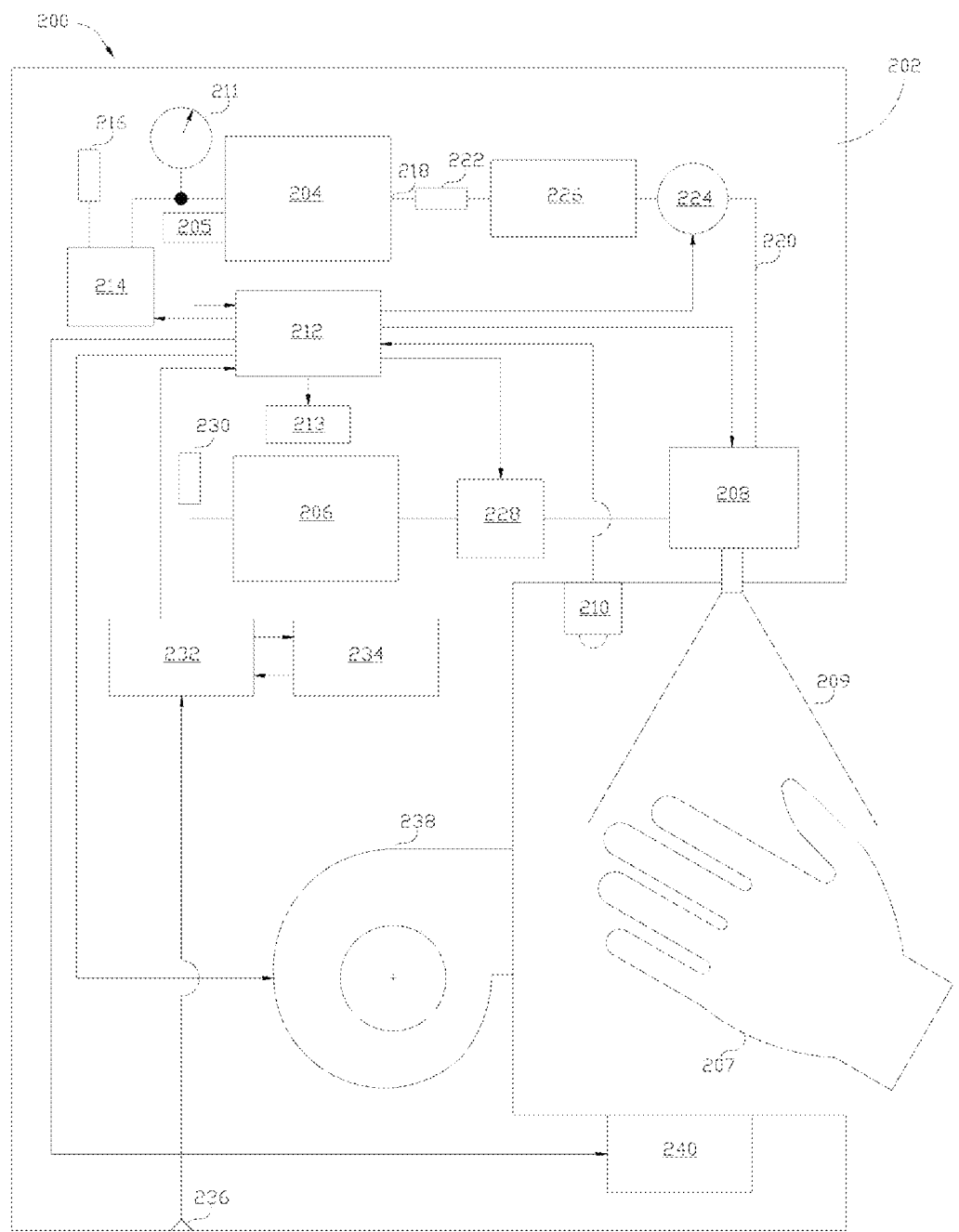

As shown in FIG. 2A, the active agent receptacle 206 can have a filter 230 associated therewith that filters out dirt and other impurities from vent air that displaces the active agent and the agent is withdrawn from the receptacle 206. The filter can be removable and replaceable.

The housing 202 can include a power supply module 232 that can draw power from a battery element 234 or from an AC power supply through an AC inlet 236. The battery element can be removable and replaceable. In some implementations, the system 200 can be portable.

The one or more nozzles of the nozzle component 208 can have a variety of different configurations, and they can be stationary or moveable. In some implementations, the system can have both stationary and moveable nozzles such that one or more of the nozzles are stationary, while one or more of the nozzles are moveable. The nozzles can be arranged in various ways so as to deliver an active agent in a desired manner. For example, the nozzles can be disposed at certain locations on a housing of the system in a manner that requires moving a hand with respect to the nozzles to ensure complete coverage of the hand with the active agent. In some examples, however, the nozzles can be disposed such that a hand can simply be positioned in proximity thereof and no additional movement of the hand is required to adequately cover the hand with the active agent provided by the nozzles. In such examples, at least a portion of the housing can be shaped such that one or more hands can be positioned to be treated with an active agent and no additional movement of the hands can be required for the treatment. This helps to ensure compliance. For example, the housing can have a cavity or other opening having nozzles openings on its inner walls. The cavity can have any suitable shape and size. As an example, the cavity can be shaped so as to conform to the shape of the hand or in other way to allow coverage of the hand without additional actions from the user after the hand has been placed into the cavity. However, it should be appreciated that the cavity can be oval, rectangular, or it can have any other shape. The cavity's size can allow it to receive one or two hands. Furthermore, in some implementations, more than one person can use the system to sanitize their hands simultaneously. The nozzles can have various sizes and shapes in order to deliver an active agent aerosol in a desired manner.

Figure 2B:
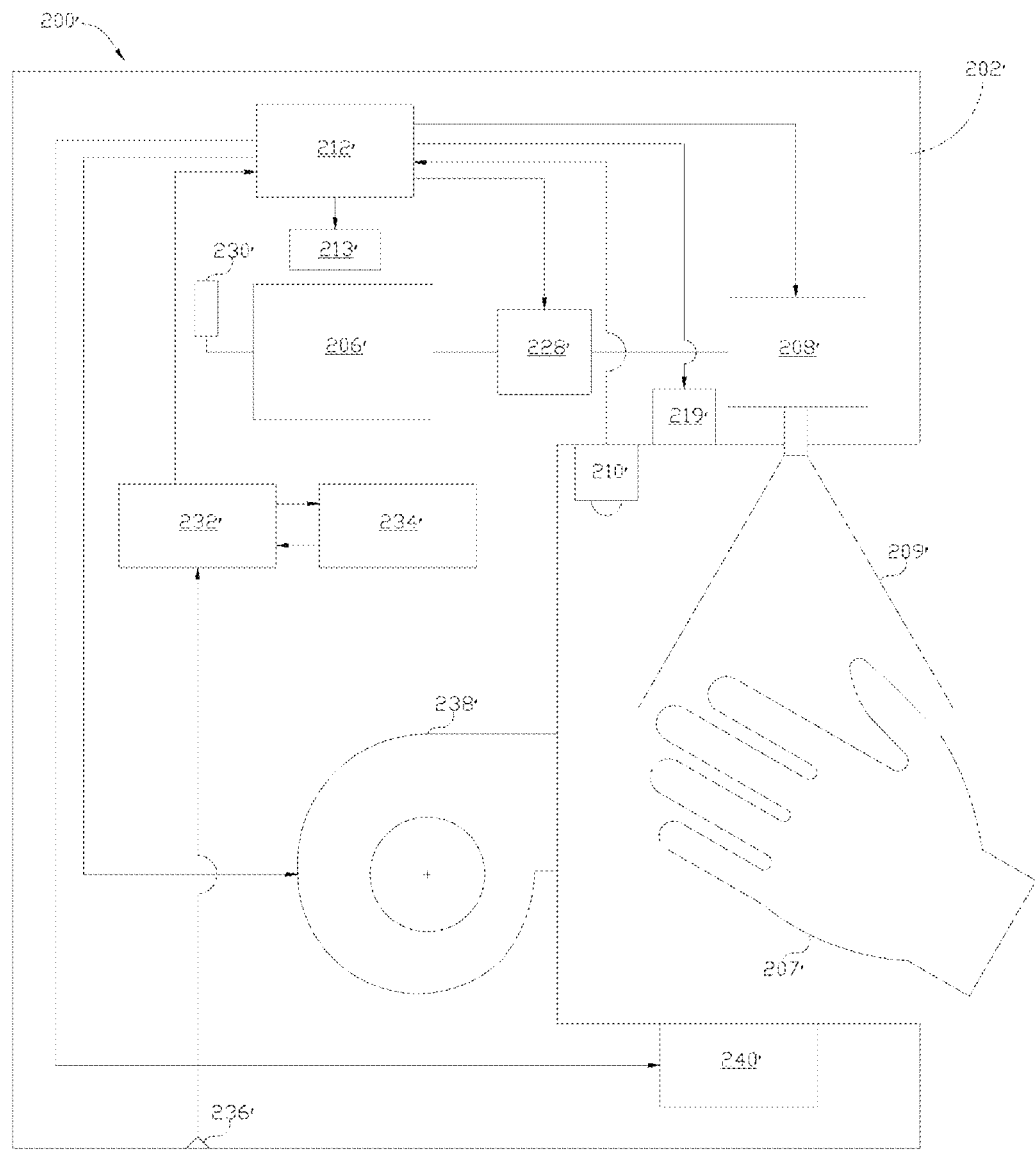
Figure 2C:
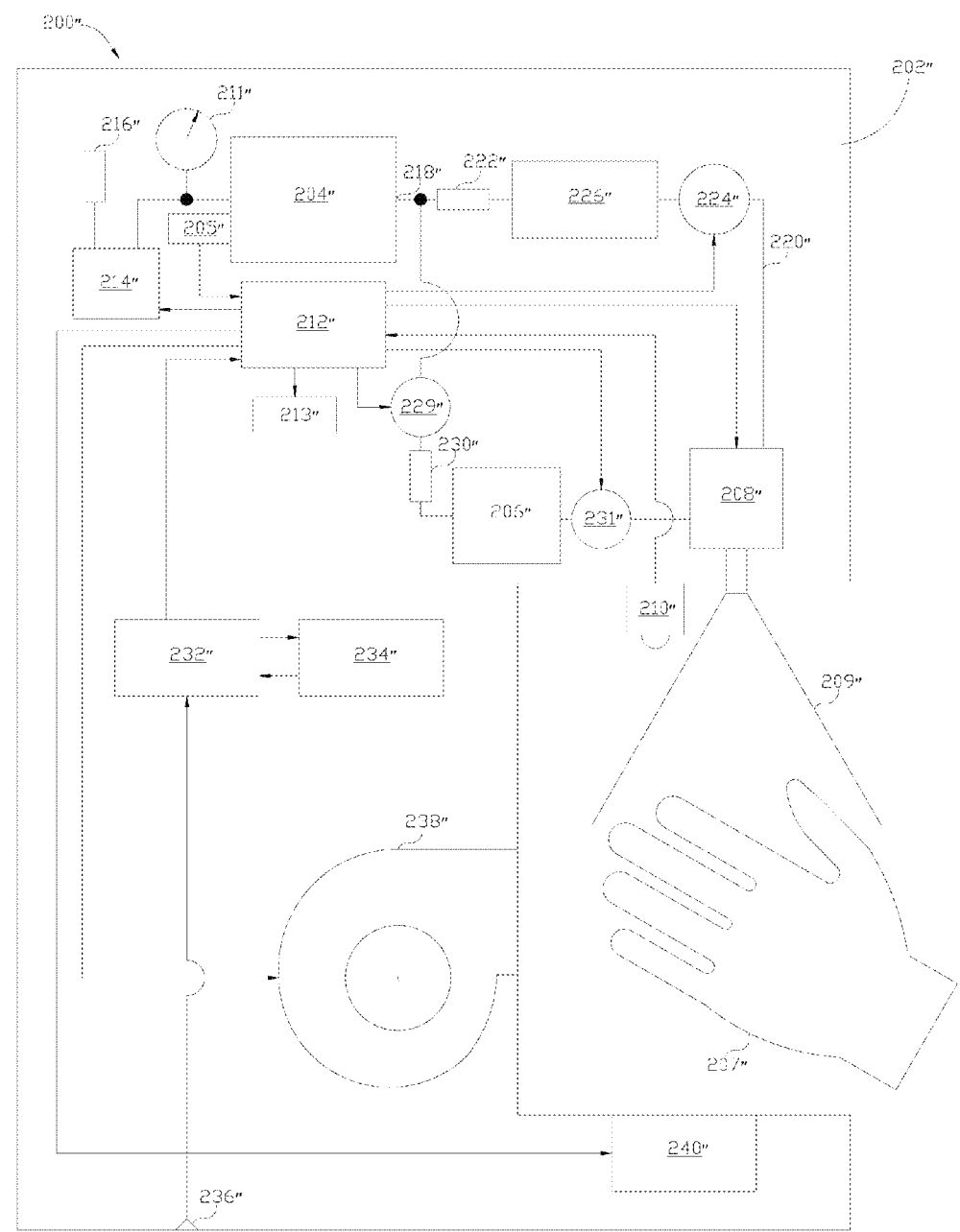
Figure 3:
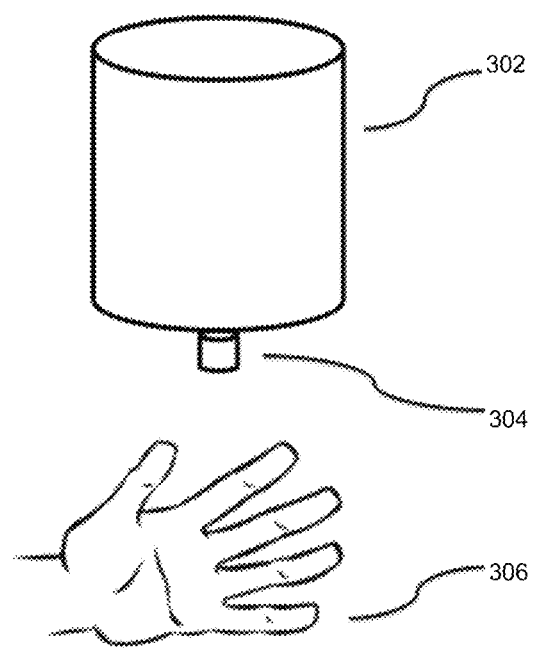

FIGS. 3, 4, and 5A-5C illustrate examples of different types of nozzles that can be used in conjunction with the system 200 or other system implementing the described techniques, e.g., system 200' (FIG. 2B) and the system 200" (FIG. 2C) described in more detail below. FIG. 3 shows an example of a portion of a system 300 implementing the described techniques. As shown, the system 300 includes a housing 302 having a single stationary nozzle 304 configured to dispense an active agent to a surface such as, in this example, a hand 306. It should be appreciated that although one user's hand 306 is shown, depending on size and configuration of the stationary nozzle 304, the nozzle 304 can deliver an active agent to sanitize both hands of the user at the same time.

FIG. 3 shows the user's hand 306 placed adjacent to the stationary nozzle 304 such that the palm-side of the hand faces the nozzle 304. In this configuration, the active agent is dispensed from the nozzle 304 and delivered to the palm-side of the hand. In order to receive the active agent on the top of the hand, the user needs to rotate his or her hand by 180 degrees such that the top of the hand faces the nozzle 304. In this configuration, the cone angle of the sprayed active agent can be designed to allow delivery to the sides of the hand and to the sides of the fingers. To ensure that these regions of the hand are not blocked (e.g., because the user has closed or bent the fingers, clenched the hands, or the hands are touching each other), the system 300 may provide an indication to the user informing the user of the requirement to keep his/her hand in an appropriate manner. For example, an indication can be provided to the user in an audio, visual, or a combination form reminding the user to position his/her hand such that the fingers are spread, the hands are not in contact with each other or other objects, etc. In addition, because a person is more likely to have his/her fingers spread if the palm of his/her hand is facing up or down (rather then sideways, as during a "handshake" position), the system can be configured such that it can receive a hand only if it is disposed with the palm facing up or down.

Figure 4:
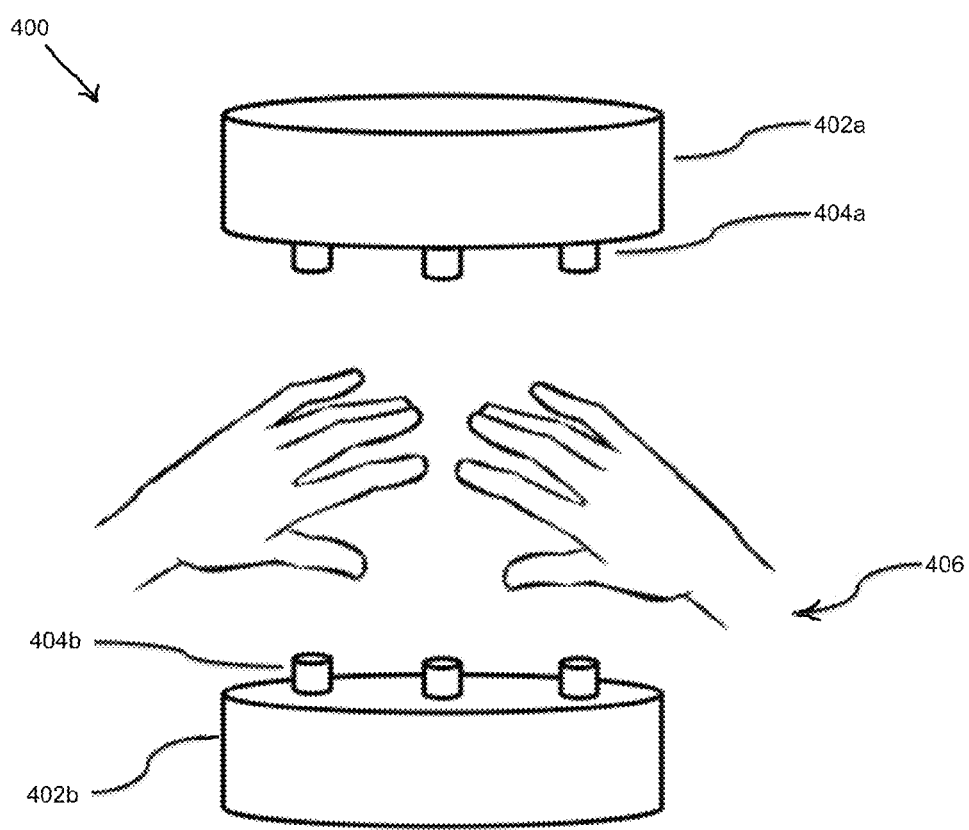

FIG. 4 shows a portion of a system 400 implementing the described techniques with nozzles having another configuration. The system 400 can have the same or similar components as those described in connection with systems 100 (FIG. 1), 200 (FIG. 2A), 200' (FIG. 2B), and 200" (FIG. 2C). In this example, the system 400 includes a housing two portions of which are shown as upper and lower housing portions 402a, 402b. As shown, the upper and lower housing portions 402a, 402b have arrays of nozzles 404a, 404b associated therewith, respectively. It should be appreciated that, even though in the system 400 each of the nozzle arrays 404a, 404b has three nozzles, the nozzle arrays can have any suitable number of nozzles (e.g., two or more than three), including a different number of nozzles among the arrays.

In the example of FIG. 4, as shown, the nozzle arrays 404a, 404b can dispense an active agent to both sides of a target surface, such as the tops and bottoms of a pair of hands 406. A person skilled in the art will appreciate that any other surface having appropriate shape and size can also be sanitized using the system 400.

The nozzle arrays 404a, 404b can have a variety of different configurations. In FIG. 4, each of the arrays is a linear array having the nozzles arranged along the same line.

It should be appreciated, however, that in one or both of the arrays the nozzles can form rectangular, circular, oval, elliptical, or other patterns.

In one embodiment, the nozzle array can be a linear strip with a micro-orifice formed as a slot along the length of the strip. The linear strip can be patterned as a serpentine layout to allow uniform delivery of micro-droplets of an active agent across an area under (or above) the serpentine layout, to the hands.

Furthermore, in some embodiments, the nozzles can be disposed and directed towards a location where a target surface is to be placed so as to form various patterns that may not necessarily be referred to as "arrays." For example, as discussed above, a housing can have a cavity or other structure having a contour conforming to a shape of a hand, and multiple nozzles can be arranged such that their orifices are disposed along inner walls of such cavity. The cavity can have an opening for a hand to be inserted therein. In such a configuration, a hand disposed within the cavity will not need to be turned or otherwise moved to be adequately covered with an active agent emitted from the nozzles which is then dried. The cavity can be shaped such that a hand can be inserted therein with the palm facing up or down, in a position which would be appropriate for a handshake, or in other manner. The cavity can also be designed such that both hands of a user can be sanitized at the same time. The cavity is positioned such that it can receive hand(s) in a convenient for a user manner. Regardless of the configuration and position of the cavity and the nozzles, the system can be configured so as to adequately sanitize at least a gripping surface of the hand(s).

Figure 5A:
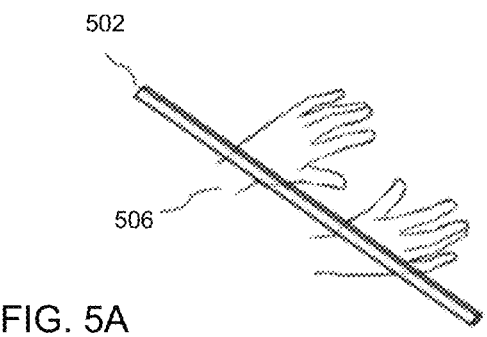
Figure 5B:
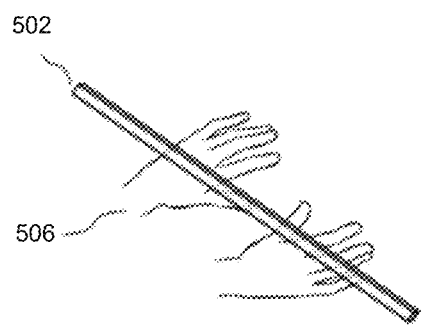
Figure 5C:
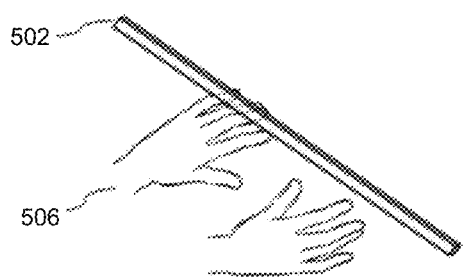

FIGS. 5A-5C illustrate schematically a moveable array of nozzles 502 (used with a sanitization system, not shown) that are configured to dispense an active agent to a pair of hands 506 to perform hand sanitization. Unlike a stationary nozzle arrangement, the moveable array moves over a surface of the hands (or any other object) during the sanitization process. In the illustrated example, the array of nozzles 502 is shown as a linear strip, though, as a person skilled in the art will appreciate, other configurations can be used alternatively. FIG. 5A shows a position of the array of nozzles 502 at a first time period, at a beginning of the hand sanitization process when the array 502 is disposed around wrists of the hands. FIG. 5B illustrates a position of the array of nozzles 502 at a second, intermediate time period of the sanitization process when the array of nozzles 502 has moved half-way with respect to the user's hands 506. Finally, FIG. 5C illustrates a position of the array of nozzles 502 at a third, later time period where the array of nozzles 502 has passed over the user's hands 506. In the example shown in FIGS. 5A-5C, the hands can be placed above or below the array 502 such that the array can scan above and below the pair of hands, thereby delivering an active agent to the tops and bottoms of the hands, where the method of delivering the active agent and drying the hands can take less than 5 seconds.

In FIGS. 3, 4, and 5A-5C, the nozzles of the respective systems are disposed such that the hand or hands are oriented with palm-sides facing "up" or "down," and where the normals to the palms are aligned with the direction of gravity. In other embodiments, the system may be configured such that the hands can be oriented with palms rotated by 90 degrees or facing the side as is conventionally achieved when shaking hands with another person One or more nozzles of a system implementing the described techniques can operate in various different ways. Thus, regardless of their particular configuration and arrangement, the nozzles can be driven using airflow-based, pressure-based, ultrasonic, or other techniques. The nozzles can have orifices of different sizes and configurations that can allow expelling an active agent as a spray having desired distribution patterns. For example, in some cases, the nozzles can provide a circular distribution of the sprayed agent on a target surface. In other cases, additionally or alternatively, the nozzles can produce a fan-shaped spray pattern relative to a stationary target object. The nozzles can be equipped with various components (e.g., air caps) that allow generating a spray having desired characteristics.

The nozzles can have various operating parameters. Thus, the nozzles can operate at a certain air pressure to provide an active agent flow rate appropriate to create a thin, uniform layer of an active agent on a target surface in a relatively short time period (e.g., less than five seconds, less than three seconds, or less than one second). The uniform thin layer is then dried on the target surface such that the total time required to sanitize the hand is less than five seconds, less than three seconds, or less than one second. For example, in one embodiment, an ultrasonic nozzle can operate at an air pressure that ranges from about 0.2 psi to about 5 psi. The active agent can be expelled from such nozzle at a flow rate of about 15 mL/min to achieve a coating thickness of about 10.0 µm in 1 second on a surface area equivalent to one side of one hand, when supplied with air at about 2 psi air pressure. In another embodiment, an air-atomizing nozzle can have an active agent flow rate of about 35 mL/min, operating at 12 psi for the atomizing air and 10 psi for the active agent. A surface of one side of one hand can be coated using such nozzle at a thickness of about 10.0 µm in less than 0.5 seconds. Air-atomizing nozzles of this type can be operated over an air pressure ranging from about 5 psi to about 100 psi, with liquid supplied over a range from about 10 psi to about 50 psi.

Referring back to FIG. 2A, as mentioned above, the housing 202 can also include an optional drying component 238 configured to dry the target surface 207 after the active agent 209 in the form of an aerosol is dispensed on the target surface 207. In this example, the drying component 238 can be an air dryer that can provide an air stream to dry a target surface after it has been treated with the active agent. The drying component 238 can have a variety of configurations. The drying component 238 can use a flow of an ambient air having room temperature or the air can be heated. Alternatively, the drying component can be an infrared heater that can provide infrared radiation to the target surface to dry it. The drying component can have any other configurations, as the described techniques are not limited in this respect. Regardless of its specific configuration, the drying component, if present, is configured to dry the thin film of an active agent deposited on a target surface.

As described above, the drying component can be controlled to dry a target surface for a predetermined time period. The time period can be preset such that the drying process continues for a predetermined duration of time, e.g., five seconds, three seconds, or other duration. As another option, a required level of dryness can depend on user's actions. In such scenarios, the drying can proceed until the system determines that the user's hand (or other surface) being sanitized is no longer in proximity to the sensor. In some embodiments, the sensor 210 or one or more other sensors that can alternatively or additionally be associated with the system can detect a dryness level of the target surface.

The sensor module 210 can also have a variety of different configurations, and it can have one or more sensors of any suitable type. The sensor of the sensor module 210 can be an optical proximity sensor that is able to detect the target object shown by way of example only as the hand 207 in FIG. 2A. The optical proximity sensor can also be able to detect a position and motion of the hand 207 or other target object. For example, the sensor can detect that the hand 207 has been disposed in proximity to the nozzle(s) 208, and it can also detect a way in which the hand 207 is positioned with respect to the nozzle(s) 208. Other events can also be detected by one or more sensors of the sensor module 210, as described below.

The active agent receptacle 206 of the system 200 can have various configurations and it can receive and store the active agent in a variety of ways. Thus, the active agent receptacle 206 can be configured as a refillable reservoir that is configured to receive a supply of the active agent. When the amount of the active agent is below a certain amount, an appropriate indication can be provided. In some embodiments, the active agent receptacle 206 houses a removable and refillable active agent-containing cartridge. The cartridge can be replaceable such that it is pre-filled with an active agent.

It should be appreciated that the system 200 in FIG. 2A is described by way of example only, as systems having other configurations can implement the described techniques. Thus, another example of a system in which the described techniques can be implemented is shown in FIG. 2B where a system 200' is configured to deliver an active agent 209' in the form of an aerosol spray to a surface 207' (e.g., unprotected or gloved hand). As shown, the system 200' includes a housing 202' having a controller 212' associated with a display 213', an active agent receptacle 206', a fluid pump 228', a nozzle component 208' having one or more nozzles, a sensor module 210' (other ways to activate the system 200' can be used additionally or alternatively), a drying component 238', a power supply module 232' that can draw power from a battery element 234' or from an AC power supply through an AC inlet 236', and an optional overspray collector 240'. These components can be similar to the corresponding components of the system 200 (FIG. 2A) and are therefore not described in more detail. The system 200' may not include air delivery components. However, in some implementations, one or more air delivery components can be present. In this example, the atomized active agent can be moved from the nozzle(s) of the nozzle component 208' to the target surface 207' by at least one (optional) fan 219'. The system 200' can be an ultrasonic atomizing system. Furthermore, the configuration of the system 200' can also be representative of a pressure-based atomizing spray system.

Yet another example of a system in which the described techniques can be implemented is shown in FIG. 2C where a system 200" is configured to deliver an active agent 209" in the form of an aerosol spray to a surface 207" (e.g., unprotected or gloved hand). As shown, the system 200" includes a housing 202" having a filter 216", a pump 214", a sensor 205", a gauge 211", an air tank 204" with an outlet 218", a filter 222", a pressure regulator component 226", a control valve 224", a controller 212" associated with a display 213", a filter 230", an active agent receptacle 206", a nozzle component 208" having one or more nozzles, a sensor module 210" (other ways to activate the system 200" can be used additionally or alternatively), a drying component 238", a power supply module 232" that can draw power from a battery element 234" or from an AC power supply through an AC inlet 236", and an optional overspray collector 240". Air is provided from the outlet 218" of the air tank 204" to the nozzle component 208" via a conduit 220". These components can be similar to the corresponding components of the system 200 (FIG. 2A) and are therefore not described in more detail in connection with FIG. 2C. In this example, the active agent is displaced from the active agent receptacle 206" by air from the air tank 204". A control valve 229" under control of the controller 212" admits pressurizing air to the receptacle 206". Dispensing of fluid from the receptacle 206" to the nozzle component 208" occurs when a control valve 231" is actuated by the controller 212".

It should be appreciated that the systems 100 (FIG. 1), 200 (FIG. 2A), 200' (FIG. 2B), 200" (FIG. 2C) are exemplary only, and that the systems 100, 200, 200', 200" can include other components that are not shown herein.

Figure 6:
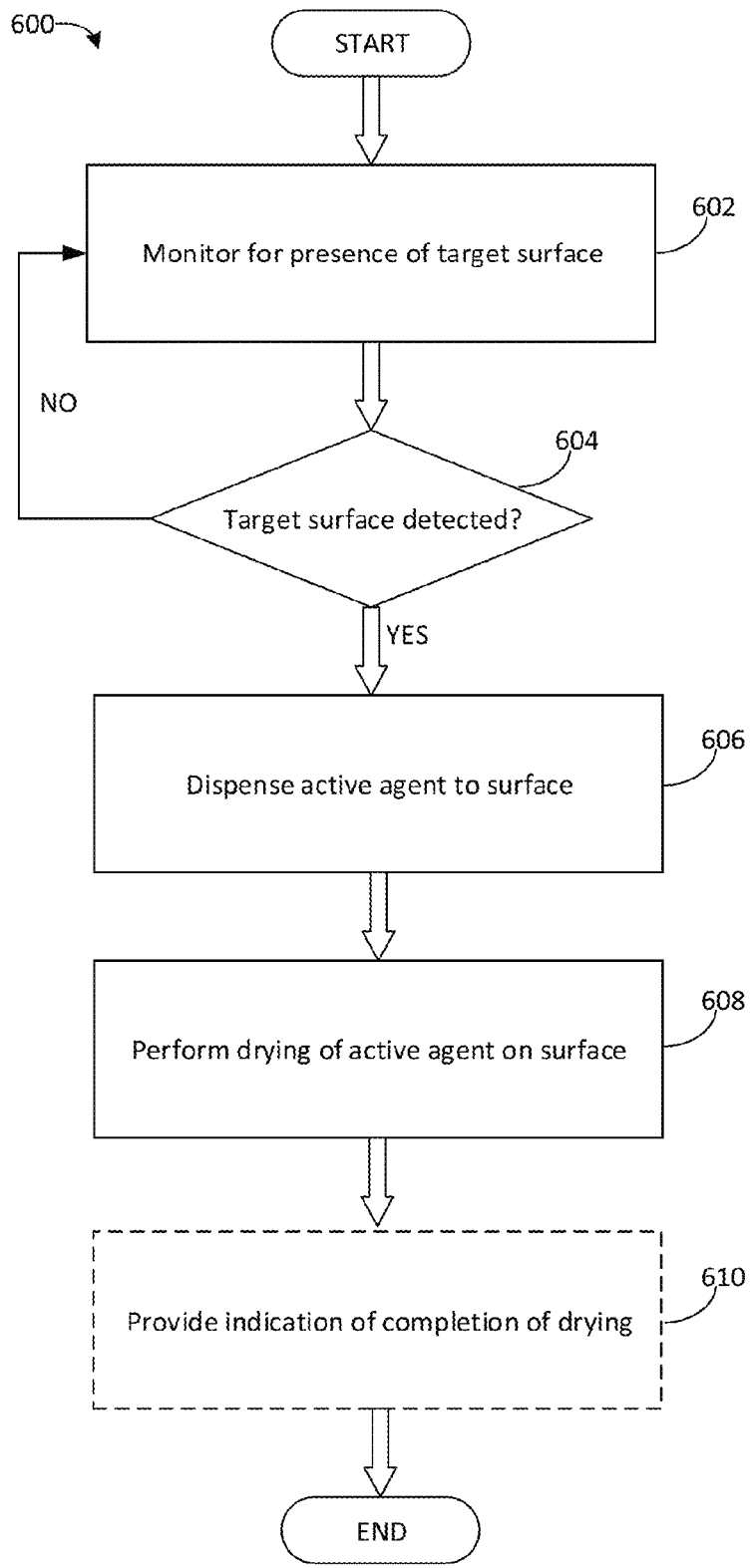

Regardless of the specific configuration of the system implementing the described techniques, the techniques provide a method of killing or inactivating transient pathogens on a surface of the skin or any other surface. FIG. 6 illustrates a process 600 of killing or inactivating transient pathogens on a surface using an active agent including one or more antiseptic or disinfectant reagents, in accordance with the described techniques. The process 600 is described herein in connection with the system 200 (FIG. 2A) as an exemplary system which can perform this process. However, it should be appreciated that the process 600 can be performed by system 100 (FIG. 1), system 200' (FIG. 2B), system 200" (FIG. 2C), or by any other suitable system.

The process 600 can start at any suitable time. For example, it can start when a system performing it (e.g., system 100 or 200) is activated. The process 600 can be controlled by a control module of a system, such as, e.g., controller 212 in FIG. 2.

At block 602, the system can monitor for presence of a target surface in proximity to system's nozzle(s) (e.g., nozzle module 208 in FIG. 2A). The target surface is considered to be "in proximity" to the nozzles when it is adjacent to the nozzles such that an active agent that can be dispensed from the nozzles can reach the surface to adequately cover it with a layer of the active agent. The target surface can be one or both of user's hands, or another object. The user's hand or hands may be bare or gloved. As discussed above, a proximity sensor, a motion sensor, or other type of a sensor can operate to determine whether a surface is detected in proximity thereof.

Also, in some embodiments, the system can be activated to perform the surface sanitizing process in other ways, which can be different from the processing at blocks 602 and 604 in FIG. 6, which are shown by way of example only. Thus, additionally or alternatively, the system can receive an instruction from a user via a suitable mechanism such as a footswitch, button, touchscreen, sensor, or any other control mechanism configured to activate the system. The control mechanism can be coupled to a system's housing (e.g., it can be attached to the housing or coupled thereto via a wired connection) or it can be a remote device wirelessly communicating with components of the housing. Thus, in some embodiments, the target surface may not be detected but rather the system is activated to perform the described techniques in response to other suitable trigger.

Regardless of the specific way in which it is determined that the target surface is in proximity to the nozzles and/or the way in which an instruction to activate the system is received, in response to determining that the target surface is adjacent to the nozzle, the process 600 continues to block 606 where the active agent is dispensed onto the target surface. The active agent can include one ingredient that can kill or inactivate a transient pathogen on the surface, or a mixture of two or more of such ingredients examples of which are discussed below. The active agent is dispensed from one or more nozzles, such as the nozzle(s) of the nozzle module 208 shown in FIG. 2. The active agent is dispensed onto the surface in the form of an aerosol spray, and forms an aerosolized layer that is a thin and substantially uniform coating on the target surface.

The layer of the active agent can be from about 1 μm to about 50 μm in thickness. Furthermore, in some embodiments, the active agent layer can be from about 5 μm to about 20 μm in thickness. In yet other embodiments, the thickness of the active agent layer can be from about 4 μm to about 10 μm.

The system can be configured to deliver the active agent such that there are no uncoated areas of the surface (or such that the uncoated areas do not affect the result of the sanitization process). The uniform coating can be achieved due to aerosol properties of the active agent. In particular, the active agent in the form of an aerosol includes small fluid droplets having a size (or a size distribution) that allows a thin uniform layer of the active agent to be formed on a target surface. In at least some embodiments, the active agent droplets can be from about 18 μm to about 56 μm in diameter. The droplets' size distribution can vary in different ways and an average diameter of the droplets can be about 33 μm in diameter. In at least some embodiments, the droplet sizes can be from about 36 μm to about 107 μm with, an average diameter of about 57 μm. In other embodiments, the droplet sizes can range from about 28 μm to about 116 μm, with an average diameter of about 59 μm. It should be appreciated that active agent droplets of other sizes can be formed additionally or alternatively. The active agent delivery process at block 606 can be controlled to ensure adequate treatment of the target surface. For example, suitable one or more sensors (e.g., sensor 210 and/or any other sensor) can monitor the agent delivery process to ensure adequate surface coverage. The sensors can determine whether any fluid is present on the target surface, as a way to control proper delivery of the active agent onto the surface. The sensor(s) can also monitor the degree of uniformity of the active agent deposition over the target surface.

If it is determined, at decision block 604, that the target surface has not been detected, the process 600 can return to block 602 to continue monitoring for the presence of the target surface, as shown in FIG. 6.

After the active agent has been dispensed onto the surface, the active agent is dried on the surface, at block 608. The drying can be performed by a suitable drying component such as, e.g., the drying component 238 (FIG. 2A). The drying can be performed by a stream of air (which can be cool or warm air), by an infrared dryer, or using any other approach. As mentioned above, the drying component is optional, and the layer of the active agent dispensed on the target surface can be dried by ambient air. For example, the user can simply wait for a few seconds for his/her hands treated with an active agent to dry.

The processing steps at blocks 606 and 608 can both be completed quickly, e.g., in less than five seconds. The dispensing of the active agent can take less than three seconds, and the drying of the agent disposed as a layer on the treated surface can take less than two seconds. However, the agent dispensing and drying steps can be performed over other periods of time. Moreover, in some embodiments, the entire process of treating a target surface can take less than three seconds. In this way, the user can have his/her hands to be sanitized in a convenient and timely manner.

Regardless of how the drying is performed, at block 610 of FIG. 6, the system can determine whether the drying is completed and provide an indication of completion of the drying step. A suitable optical sensor can monitor the target surface being treated and it can determine when the surface is considered to be sufficiently dry. For example, the sensor can be used to automatically determine whether there are any moist areas present on the surface and to determine a dryness level of the surface. The indication can be provided to the user in audio, visual, or other forms. For example, an audio signal can be generated to indicate to the user that his/her hands have been sanitized. As another option, additionally or alternatively, a visual indication (e.g., a light indicator, a textual message, or other indication) can be presented to a user on a display, such as, e.g., display 213 in FIG. 2A. In addition, a suitable indication can be provided to a user during the active agent application and/or drying. For example, an indicator of one color can be provided while the process is in progress, and the color can change once the process is completed. Also, in some embodiments, no indication of completion of drying is provided and the user can perceive that his/her hands are dry.

Regardless of the way in which the drying is performed, the active agent on the hands' surface is effective to kill or inactivate transient pathogens on that surface. Moreover, because of the way in which the active agent is dispensed onto the hands, the active agent can sanitize the skin without significantly affecting resident microflora of the skin. In addition, even if the active agent belongs to a class of strong disinfectants that would otherwise be considered harsh to the skin (but that are nevertheless desired for use in certain settings), the quick application of a thin layer of the active agent using the described techniques allows to reduce the negative affects of such strong disinfectants.

After the indication of completion of drying is provided, the process 600 can end. It should be appreciated, however, that the process 600 can be continuous. In this way, after one surface has been treated, the system monitors for the presence of another surface in proximity to the nozzles, and/or waits for a trigger to initiate dispensing of the active agent. For example, in a hospital setting, an apparatus performing the process 600 can, in a rapid sequence, sanitize the hands of multiple personnel.

FIG. 7 illustrates another example of a process of killing or inactivating transient pathogens on a surface in accordance with the described techniques. The process 700 shown in FIG. 7 is similar to process 600 of FIG. 6 and can similarly be performed by a system such as system 100 (FIG. 1), system 200 (FIG. 2A), system 200' (FIG. 2B), system 200" (FIG. 2C), or by other suitable system. The process 700 is described here by way of example only as being performed by system 200 of FIG. 2A. Also, steps of the process 700 that are similar to corresponding steps of process 600 are not described in detail in connection with FIG. 7.

As shown in FIG. 7, after the process 700 starts at a suitable time, presence of a target surface can be detected at block 702. As discussed above, the target surface can be detected by one or more suitable sensor(s), or the system performing the current process can respond to a suitable trigger, such as an instruction to activate the nozzle. In some implementations, sensors used may be able to determine one or more properties of the detected surface, such as its size and contours.

When the target surface is detected, at block 704, airflow with regulated pressure is provided to the nozzle. For example, as shown in the example of FIG. 2A, air from the air tank 204 can be caused, by the air pump 214, to be provided to the nozzle component 208. This process is controlled by a control module (e.g., controller 212 in FIG. 2A). Air can be delivered to the nozzle module at a desired airflow pressure. The pressure of the airflow is selected such that it is sufficiently high to quickly cover a surface being treated, but at the same time not excessively high, since high pressure can generate an aerosol stream that is deposited as a layer which is thicker than desired. In embodiments in which an ultrasound atomizer is used to generate the aerosol, a lower pressure can be used, e.g., from about 0.5 psi to about 5 psi. In other embodiments in which an airflow-based atomizing spray system is used, a higher pressure can be used, e.g., greater than about 5 psi.

At block 706, as shown in FIG. 7, at least one nozzle of the system performing the process is activated. A dosage of the active agent can be provided to the activated nozzle at block 708. Referring again by way of example only to system 200 in FIG. 2A, the active agent can be provided, by the fluid pump 228, from the active agent receptacle 206, to the nozzle component 208.

The dosage can be selected based on expected surface of the target surface to be sanitized, which can be done in advance (e.g., if the nozzles are used to spray surfaces of similar sizes) or the dosage can be selected dynamically, based on properties (e.g., size, contours, etc.) of the specific target surface being treated. For example, in embodiments where the system is configured to disinfect hands, the dosage can be selected based on the size of the area of one or both hands. In the case of an individual hand, where the surface area is about 500 cm$^2$, a dispensed dose of 0.5 mL of an active agent uniformly distributed across this hand surface would yield a coating about 10 µm thick. An active agent dose of 3 mL dispensed uniformly across the same surface area would yield a coating about 60 µm thick. Allowing for a 30% overspray (excess active agent that spreads beyond the target surface being sprayed), the 3 mL dosage can be increased to about 4 mL to yield a 60 µm thick coating. Uniform coating of two hands with a 60 µm thick coating and a 30% overspray would require a dosage of about 8 mL. In cases where only the palms and adjacent finger surfaces of a pair of hands are treated, a 30% overspray is expected and the target coating thickness is about 10 µm thick, the dosage of the active agent can be about 1.5 mL.

At block 710, the dosage of the active agent is dispensed from the nozzle so as to form a thin uniform layer on the target surface. As discussed above, the active agent is dispensed in the form of an aerosol spray. The aerosol spray can be created by an air atomizing nozzle that uses air pressure to create the spray, as well as to deliver the droplets of the spray to the target surface. In other embodiments, the system can be an ultrasonic nozzle system. In yet other embodiments, the system can use hydraulic nozzles. A positive-displacement pump, a suction- or pressure-based fluid delivery approach, or any other suitable approach can be used to deliver fluid to the nozzle or nozzles. As an example, in the system 200 of FIG. 2A, the aerosol is created by aerosolizing the active agent received from the active agent receptacle 206 in the airstream delivered to the nozzle via the conduit 220.

After the target surface is sprayed with the desired dosage of the aerosolized active agent, a drying component is activated to dry the active agent on the surface, at block 712. An indication of completion of the drying process, and therefore completion of the surface sanitization, is provided at block 714. The process 700 can then end, though it can be performed continuously, to sanitize another target surface.

The active agent can include one or more ingredients that can be used to inactivate or kill transient pathogens on a target surface such as a surface of the hand. Any one or more pathogen inactivation fluids or germicidal fluids can be used in the active agent. The active agent is selected such that it can be delivered onto a target surface as a thin, uniform, quick-drying coating capable of quickly killing or inactivating transient pathogens on the target surface.

As an example, the active agent can be an aqueous solution of hypochlorous acid. Any suitable source of hypochlorous can be used. For example, Excelyte (Integrated Environmental Technologies, LTD., Little River, S.C.) or another suitable source of hypochlorous acid can be used. Excelyte can be given as a possible aqueous hypochlorous acid composition, since it is reported (according to the package label) to be effective at killing *Clostridium difficile, Escherichia coli*, MRSA, *Salmonella, Pseudomonas, Listeria monocytogenes, Enterococcus faecalis* (VRE), *Klebsiella pneumonia* (NDM-1) and *Staphylococcus aureus*. The aqueous solution of hypochlorous acid can have any suitable concentration of hypochlorous acid. In some embodiments, the aqueous solution of hypochlorous acid includes at least about 0.046% of hypochlorous acid. As another example, the aqueous solution of hypochlorous acid can include from about 0.005% to about 1% of hypochlorous acid. A suitable commercial product or a solution thereof can be used as an active agent.

As another example, the active agent can be an aqueous solution of hydrogen peroxide used as a pathogen inactivation or germicidal fluid, since hydrogen peroxide is a broad spectrum antimicrobial capable of inactivating or killing bacteria, viruses, fungi and spores. The aqueous solution of hydrogen peroxide can include about 0.3%, about 1%, about 3%, about 6%, about 9% or about 12% of hydrogen peroxide. In some embodiments, the aqueous solution of hydrogen peroxide can be used with hydrogen peroxide concentration in the range from about 3% to about 6%.

As another example, the active agent can be accelerated hydrogen peroxide or AHP. AHP is a proprietary blend of hydrogen peroxide, surface active agents, wetting agents, chelating agents and water designed for improved germicidal potency and cleaning performance (Virox, Oakville, ON, Canada). AHP is used as a pathogen inactivation or germicidal fluid since it is a broad spectrum antimicrobial capable of inactivating or killing bacteria, viruses, fungi and spores and is expected to readily wet the surfaces of the hands, allowing for the development of a thin, uniform coating from a controlled spray of micro-droplets of AHP onto the hands. When the active agent is an aqueous solution of hydrogen peroxide, the aqueous solution of hydrogen peroxide can be used with hydrogen peroxide concentration in the range from about 3.0% to about 12.0%.

As another example, the active agent can be an aqueous solution that is a mixture of peracetic acid and hydrogen peroxide.

As yet another example, the active agent can be an aqueous solution of acetic acid. The aqueous solution of can have acetic acid concentration in the range from about 1% to about 10.0%. In other embodiments, the aqueous solution of acetic acid used can have acetic acid concentration in the range from about 3.0% to about 6.0%. An aqueous solution of acetic acid is used as a pathogen inactivation or germicidal fluid when broad spectrum bacterial inactivation or killing is warranted.

In some embodiments, the active agent can include an aqueous solution of isopropyl alcohol. The aqueous solution of isopropyl alcohol can have isopropyl alcohol concentration from about 60% to about 90%.

In some embodiments, the active agent can include an aqueous solution of ethanol. The aqueous solution of ethanol can have ethanol concentration from about 60% to about 90%.

In another embodiment, the active agent can include an aqueous solution of peracetic acid. The aqueous solution of peracetic acid can have peracetic acid concentration from about 0.1% to about 1.0%.

In other embodiment, the active agent can include an aqueous solution of sodium hypochlorite. The aqueous solution of sodium hypochlorite can have sodium hypochlorite concentration from about 0.1% to about 1.0%.

Regardless of the specific ingredient or a mixture of ingredients included in the active agent, the process of spraying a small volume of the active agent, followed by rapid drying of the hands, has the effect of reducing the numbers of viable transient bacteria on the surfaces of the hands. This thin, uniform coating of fluid is quickly dried by exposure to the ambient environment or using "active" techniques such as, e.g., a stream of forced air, forced heated air, or infrared radiation. The act of drying stops or substantially reduces the pathogen inactivation or killing process thereby limiting the microbial inactivation or killing to the transient pathogens on the outermost surface of the skin. The sanitization process has the effect of inactivating or killing transient pathogens on the surfaces of the hands, which can be done without substantially altering the resident microflora population or causing irritation or toxic effects on the skin.

In at least some embodiments, the active agent can also be an aqueous solution of ozone having ozone concentration in the range from about 1 parts per million (ppm) to about 40 ppm. In at least some embodiments, the ozonated water can have dissolved ozone concentration from about 0.2% to about 2.0%. Further, in at least some embodiments, the active agent can also be an aqueous solution of ozone having dissolved ozone concentration in the range from about 0.1 mg/L to about 10 mg/L. An aqueous solution of ozone can be used as a pathogen inactivation or germicidal fluid since ozone is a broad spectrum antimicrobial capable of inactivating or killing bacteria, viruses, fungi and spores.

The active agent can also be a mixture of aqueous solutions of ozone (i.e., ozonated water) and hydrogen peroxide. In some embodiments, the ozonated water and aqueous hydrogen peroxide can be delivered to hands as a target surface from separate nozzles. These nozzles and the spraying protocols can be designed to provide mixing of the ozonated water and aqueous hydrogen peroxide within the delivered spray or upon impingement onto the skin surface. In other embodiments, the ozonated water and aqueous hydrogen peroxide can be mixed within the delivery apparatus prior to spraying through the same nozzle or array of nozzles. Regardless of whether the ozonated water and aqueous hydrogen peroxide are delivered together or separately to the target surface, a thin, uniform coating of the active agent delivered onto the surface of the hands is quickly dried by exposure to the ambient environment or using "active" techniques such as, e.g., a stream of forced air, forced heated air, or infrared radiation.

The following non-limiting examples describe experiments that were conducted to assess efficacy of the described techniques.

The following examples are put forth so as to provide those of ordinary skill in the art with examples of how the systems, compositions, devices and/or methods described herein can be made and evaluated, and are intended to be purely exemplary of the present disclosure and are not intended to limit the scope of the disclosure. Thus, the examples below are merely illustrative of techniques for sanitizing hands or other surfaces in various settings.

EXAMPLES

Example 1

This example describes inactivation of bacteria on human hands from a brief spray of pathogen inactivation fluid followed by rapid drying.

Figure 8:
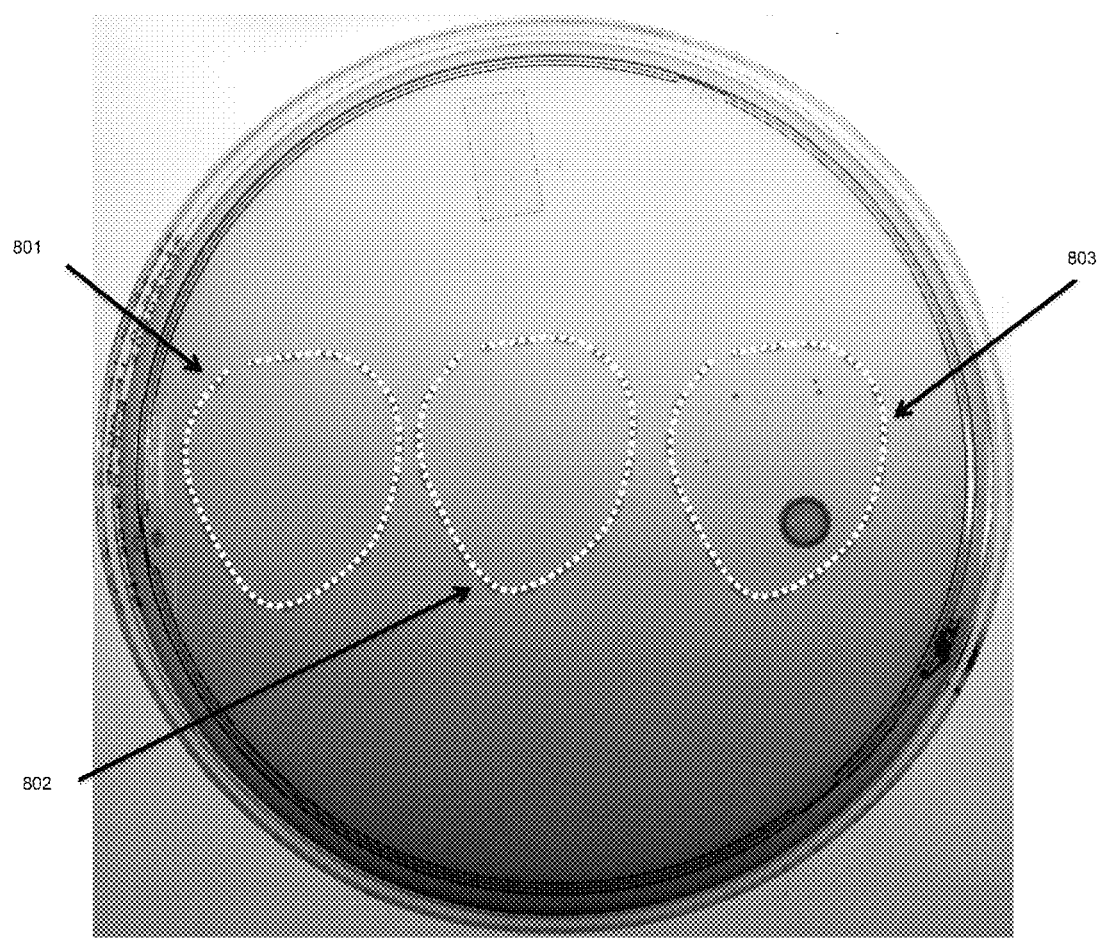

An original solution of the K-12 strain of *Escherichia coli* was obtained (Carolina Biological Supply Company, Burlington, N.C.) and diluted 10,000-fold in nutrient broth (Carolina Biological Supply Company, Burlington, N.C.) to generate a dilute bacterial solution. In this example, 25 µL of the dilute solution was pipetted onto the pads of the index, middle and ring fingers of a human hand. After pipetting, the solutions were spread with a pipette tip and allowed to dry under a small blower (Delta model BFB0712HH-A, Digi-Key, Thief River Falls, Minn.) for a few minutes. It is estimated that this 25 µL solution contained between 70 and 100 bacteria, based on bacterial plate counts from this same batch of solutions, described in Example 4 below. Just after drying, an aqueous solution of hydrogen peroxide (3.0% concentration) was sprayed for 1 second onto the middle and ring finger pads of the previously *Escherichia coli* treated index, middle and ring fingers. The spraying apparatus included an air brush (Patriot Model 105, Badger, Franklin Park, Ill.) that is capable of spraying thin coatings of a wide variety of fluids with viscosities similar to water. The index finger also previously treated with the *Escherichia coli* dilute solution was not sprayed with the aqueous solution of hydrogen peroxide. After spraying the hydrogen peroxide solution, the middle and ring finger pads were dried under the same small blower for 5 seconds. All three finger pads were then depressed onto a pre-cast Luria broth (LB) agar plate (Carolina Biological Supply Company, Burlington, N.C.). FIG. 8 shows this agar plate after an overnight incubation at 37° C. This plate shows at least 5 bacterial colonies that have grown on the region (803) of the agar that was contacted with the non-sprayed index finger pad. No bacterial colonies are seen to have grown on the regions of the agar plate that were contacted with the middle (801) and ring (802) finger pads that had been quickly sprayed with a pathogen inactivation or killing fluid and dried with a small volume of forced air.

Example 2

This example describes inactivation of bacteria on human hands from a brief spray of pathogen inactivation fluid followed by rapid drying.

A solution of the K-12 strain of *Escherichia coli* was obtained and diluted 10,000-fold in nutrient broth to generate a dilute bacterial solution. All biological supplies were sourced from Carolina Biological Supply Company (Burlington, N.C.). In this example, 5 µL of this dilute solution was pipetted onto the pads of the index, middle and ring fingers of a human hand. After pipetting, the solutions were spread with a pipette tip and allowed to dry over a few minutes under the small blower as described in Example 1. It is estimated that this 5 µL solution contained between 15 and 20 bacteria, based on bacterial plate counts from this same batch of solutions, described in Example 4. Just after drying, an aqueous solution of hydrogen peroxide (3.0% concentration) was sprayed for 1 second onto the middle and ring finger pads of the previously *Escherichia coli* treated index, middle and ring fingers. The spraying apparatus was the air brush described in Example 1. The index finger also previously treated with the *Escherichia coli* dilute solution mately 15.3 Cubic Feet per Minute (CFM) (according to the manufacturer's specifications) impinging on the disk for 5 seconds, after which the weight of the membrane was measured again.

The results are listed in Table 1:

TABLE 1

Weight measurements to assess amount of water deposited and amount of water removed after 5 seconds of active drying. Weight after drying was assumed to be at least equal to the value of the initial weight, for calculation of weight of water removed.

Figure 9:
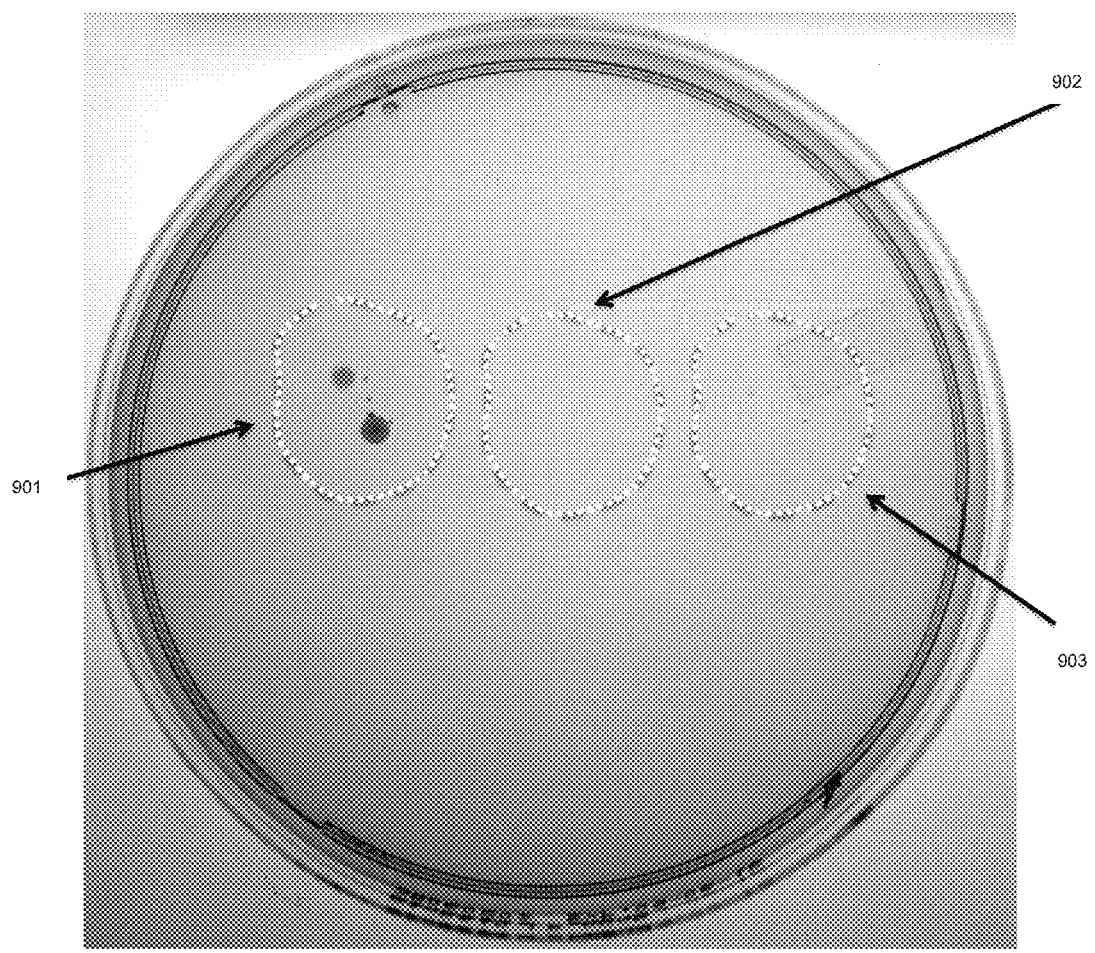

| Initial weight (mg) | Weight after spraying (mg) | Weight of water deposited (mg) | Weight after drying (mg) | Weight of water removed (mg) |
|---|---|---|---|---|
| 8.5 | 9.3 | 0.8 | 8.5 | 0.8 |
| 8.5 | 10.3 | 1.8 | 8.7 | 1.6 |
| 8.6 | 10.4 | 1.8 | 8.9 | 1.5 |
| 8.6 | 10.0 | 1.4 | 8.4 | 1.4 |
| 8.6 | 9.5 | 0.9 | 8.6 | 0.9 |
| 8.6 | 9.6 | 1.0 | 8.4 | 1.0 |
| 8.6 | 9.9 | 1.3 | 8.6 | 1.3 | was not sprayed. After spraying the hydrogen peroxide solution, the middle and ring finger pads were fully dried under the same small blower for 5 seconds. All three finger pads were then depressed onto a pre-cast Luria broth (LB) agar plate. FIG. 9 shows this agar plate after an overnight incubation at 37° C. This plate shows at least 6 bacterial colonies that have grown on the region (901) of the agar that was contacted with the non-sprayed index finger pad. No bacterial colonies are seen to have grown on the regions of the agar plate that were contacted with the middle (902) and ring (903) finger pads that had been quickly sprayed with an aqueous solution of hydrogen peroxide and dried with a small volume of forced air.

Example 3

This example describes tests to determine the amount of water deposited with an airflow-based atomizing spray system and dried with a small blower.

The quantity of water deposited from an airbrush and the amount of drying taking place in 5 seconds of exposure to airflow from a small blower were assessed on a 25 mm diameter track-etched polycarbonate membrane with 0.4 um diameter pores (Whatman Cyclopore Model 7060-2504, Sigma-Aldrich, St. Louis, Mo.). The airbrush and the small blower used in this example are described in Example 1. The initial weight of the membrane was measured using a precision balance (Sartorius Model CPA64, Bohemia, N.Y.). Following the initial weighing, the membrane was placed on a polycarbonate support block and retained by the weight of a polycarbonate plate, containing three bored-through 16.3 mm diameter holes. The plate was placed so that one of the through-holes was concentric with the membrane. The membrane was then thinly coated with water through the hole in the retaining plate, using the Badger spray brush for approximately 1 second. The plate was immediately removed to allow the membrane to be placed on the balance for weighing. After the reading was obtained, the membrane was placed in a different location on the support block and held down again with the retaining plate, but aligned with a different through-hole. This was done to prevent any water remaining on the retaining plate or support block from wicking onto the test disk. The small blower was then held a few inches above the membrane with the airflow approxi- Based on the spray area and the amount of water deposited on this area, the calculated thickness of the water deposited ranges from about 3.8 micrometers to about 8.6 micrometers. The majority of the deposited water could be removed in 5 seconds by drying in a flow of air on the top surface of the membrane.

Example 4

This example describes the development of controls for subsequent spraying and drying studies.

A solution of the K-12 strain of *Escherichia coli* was obtained and diluted 10,000-fold, 100,000-fold and 1,000,000-fold in nutrient broth to produce three dilute bacterial solutions. All biological supplies were sourced from Carolina Biological Supply Company (Burlington, N.C.). Three track-etched polycarbonate membranes (Whatman Nucleopore, Sigma-Aldrich, St. Louis, Mo.), each 25 mm in diameter with 0.4 µm pores, were placed on a vacuum manifold (Millipore, Bedford, Mass.). With the vacuum draw operating, 150 µL of one of the dilute bacterial solutions was pipetted onto the center of the exposed (matte) surface of each of the polycarbonate membranes. The solution was quickly pulled through the track-etched membrane, leaving the deposited bacteria on the exposed (matte) surface. After 5 minutes of drying on the vacuum manifold, the membranes were prepared for the next step in this experiment.

Figure 10:
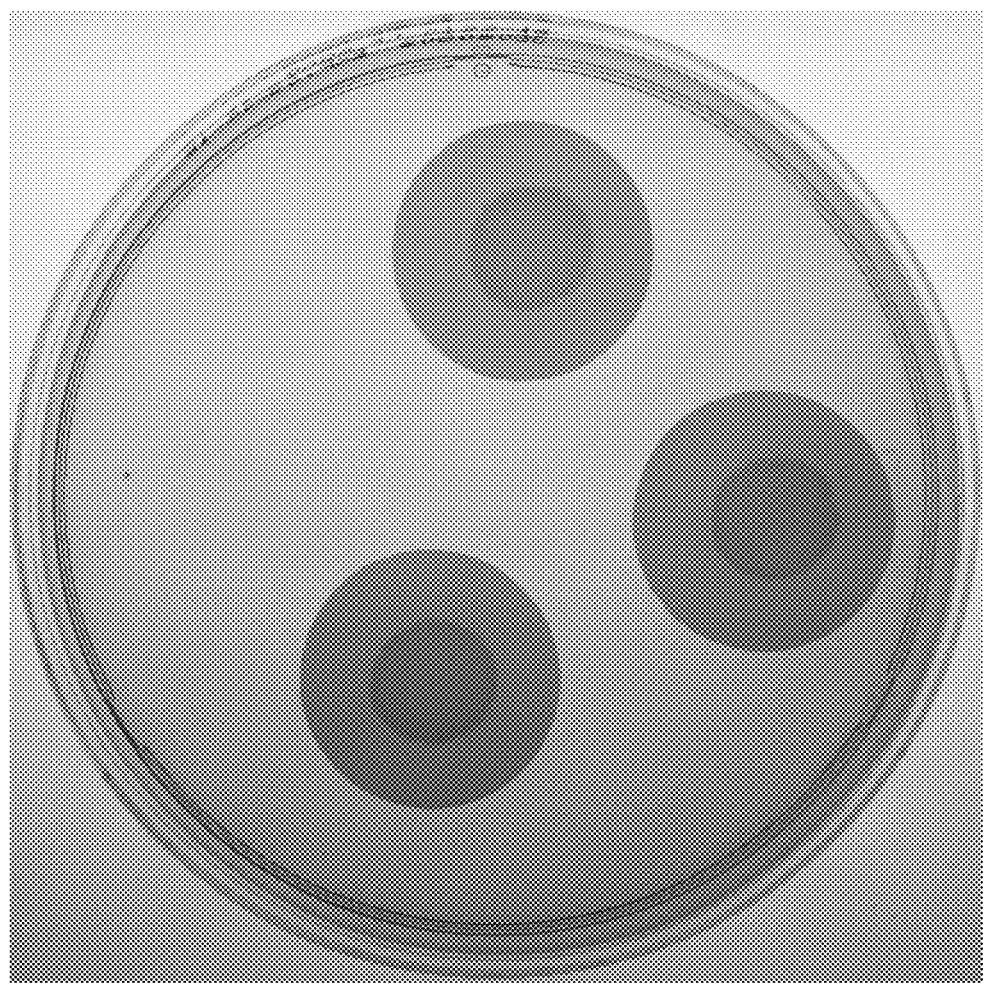

A first set of controls used the 10,000-fold dilution of the as-received (original) solution of *Escherichia coli* for the deposition step. For this set of controls, the membranes were placed matte side up, onto a pre-cast Luria broth (LB) agar plate, directly after the bacterial deposition and drying step on the vacuum manifold. The pores of the track-etched membrane allow transport of nutrient from the agar to the bacteria deposited on the matte side of the membrane. FIG. 10 shows these three membranes on the agar plate after overnight incubation at 37° C. FIG. 10 also shows full circular lawns of bacterial colonies in the center of each membrane where the 150 µL of dilute bacterial solution had previously been deposited. This experiment establishes that bacteria can be deposited onto polycarbonate membranes, dried and allowed to grow on agar via overnight incubation.

The following experiments involved spraying water onto the bacteria-deposited membranes followed by drying with a small blower. For these experiments, spraying was performed for approximately 1 second using an airbrush and drying was accomplished by holding the membrane near the output of the small blower for approximately 5 seconds. The airbrush and the small blower used for this example are described in Example 1. The spray action is estimated to have delivered a uniform coating, based on the observed reflective sheen on top of each membrane after each spray. After 5 seconds of drying with the small blower, the membranes appeared to be cleared of all fluid and fully dried.

Figure 11:
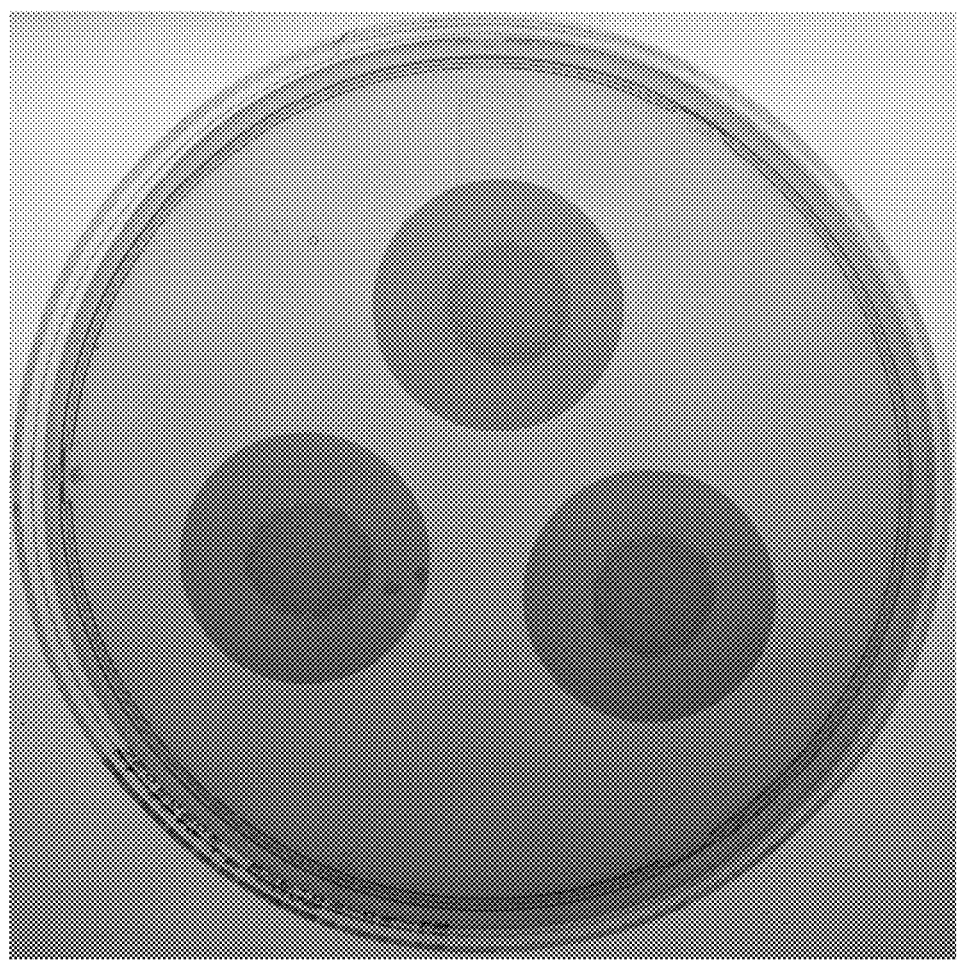

A second set of controls used the 10,000-fold dilution of the as-received solution of Escherichia coli for the deposition step, but instead of directly placing the membranes onto an agar plate, the membranes remained on the vacuum manifold and were then sprayed with water, were removed, and dried for 5 seconds with forced air from the small blower, before being placed onto the agar plate. FIG. 11 shows these three membranes on the agar plate after overnight incubation at 37° C. FIG. 11 also shows full circular lawns of bacterial colonies in the center of each membrane where the 150 µL of dilute bacterial solution had previously been deposited.

Figure 12:
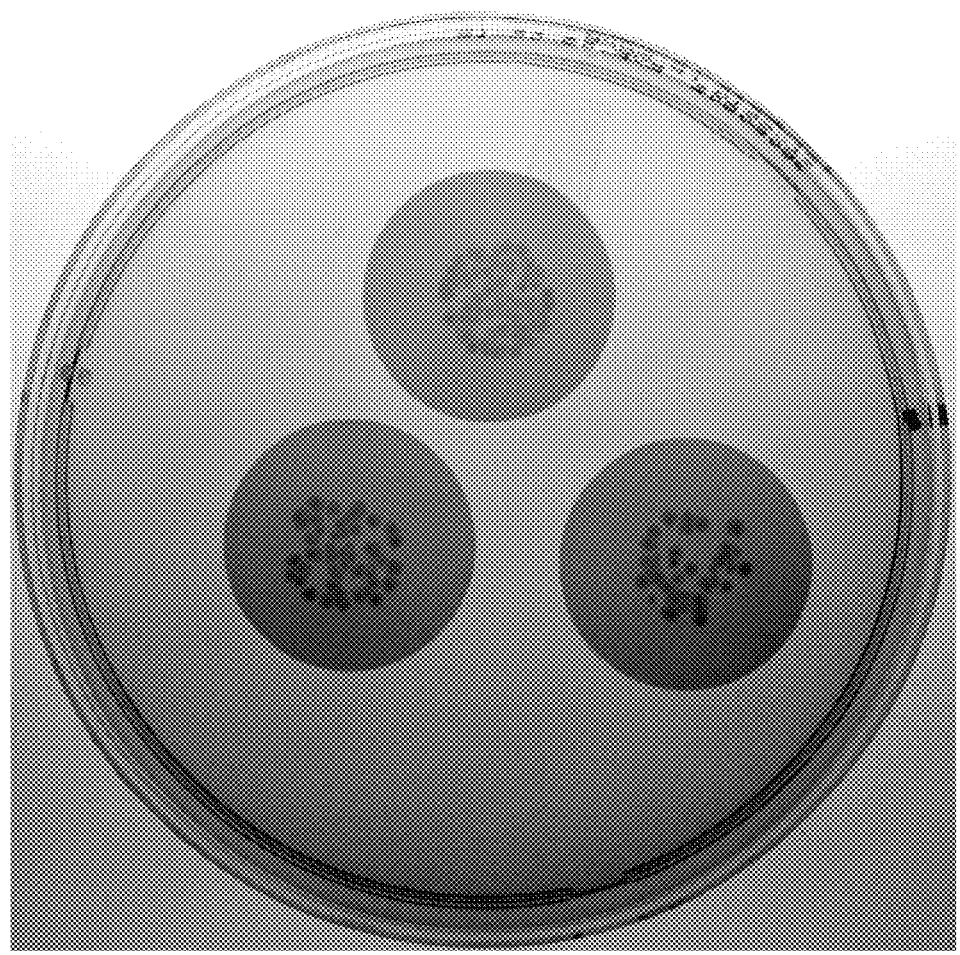

A third set of controls used the 100,000-fold dilution of the as-received solution of Escherichia coli for the deposition step. After bacterial deposition and drying, the membranes remained on the vacuum manifold and were then sprayed with water, were removed, and dried for 5 seconds with the forced air from the small blower, before being placed onto the agar plate. FIG. 12 shows these three membranes on the agar plate after overnight incubation at 37° C. FIG. 12 also shows approximately 50, 65 and 40 bacterial colonies in the centers of the three membranes, where the 150 µL of dilute bacterial solution had previously been deposited.

Figure 13:
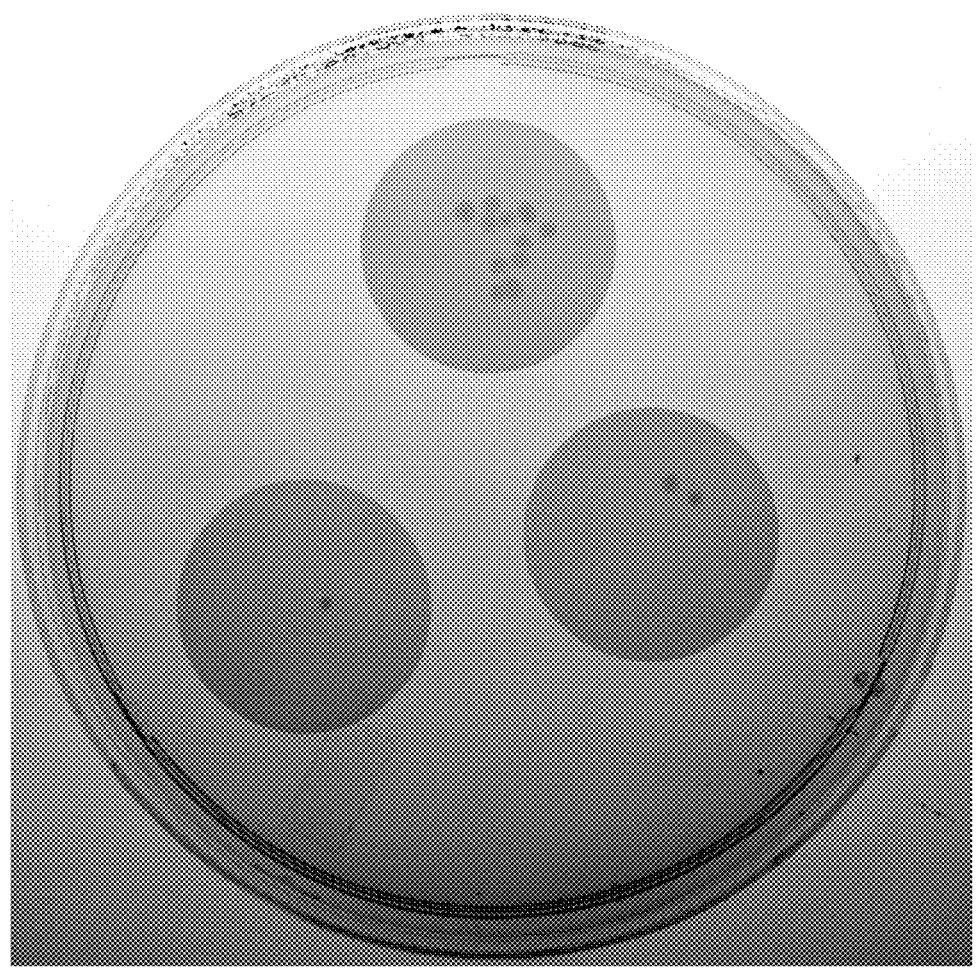

A fourth set of controls used the 1,000,000-fold dilution of the as-received solution of Escherichia coli for the deposition step. After bacterial deposition and drying, the membranes remained on the vacuum manifold and were then sprayed with water, were removed, and dried for 5 seconds with the forced air from the small blower, before being placed onto the agar plate. FIG. 13 shows these three membranes on the agar plate after overnight incubation at 37° C. FIG. 13 also shows 1, 2 and 11 bacterial colonies in the centers of the three membranes, where the 150 µL of dilute bacterial solution had previously been deposited.

These experiments establish that a dilute solution of bacteria can be deposited onto polycarbonate membranes, dried, sprayed with water, air-dried and allowed to grow on agar via overnight incubation. The average bacterial colony counts on membranes from the fourth (1,000,000-fold dilution) set of controls is 5. The average bacterial counts on membranes from the third (100,000-fold dilution) set of controls is 51. Based on these counts, it is expected that approximately 500 bacteria are deposited with 150 µL of the 10,000-fold dilution of the as-received Escherichia coli solution.

Example 5

This example describes the inactivation of bacteria on polycarbonate membranes from a brief spray of a dilute aqueous solution of hydrogen peroxide (3%), followed by rapid drying. For these experiments, the deposition of bacteria onto polycarbonate membranes followed by spraying the hydrogen peroxide solution and drying the membrane with forced air, was performed using the materials, equipment and methods described in Example 4.

A first set of membranes were prepared by depositing 150 µL of the 10,000-fold dilution of the as-received solution of Escherichia coli. Using the guidance from Example 4, it is estimated that 500 bacteria were deposited onto each of these membranes.

Figure 14:
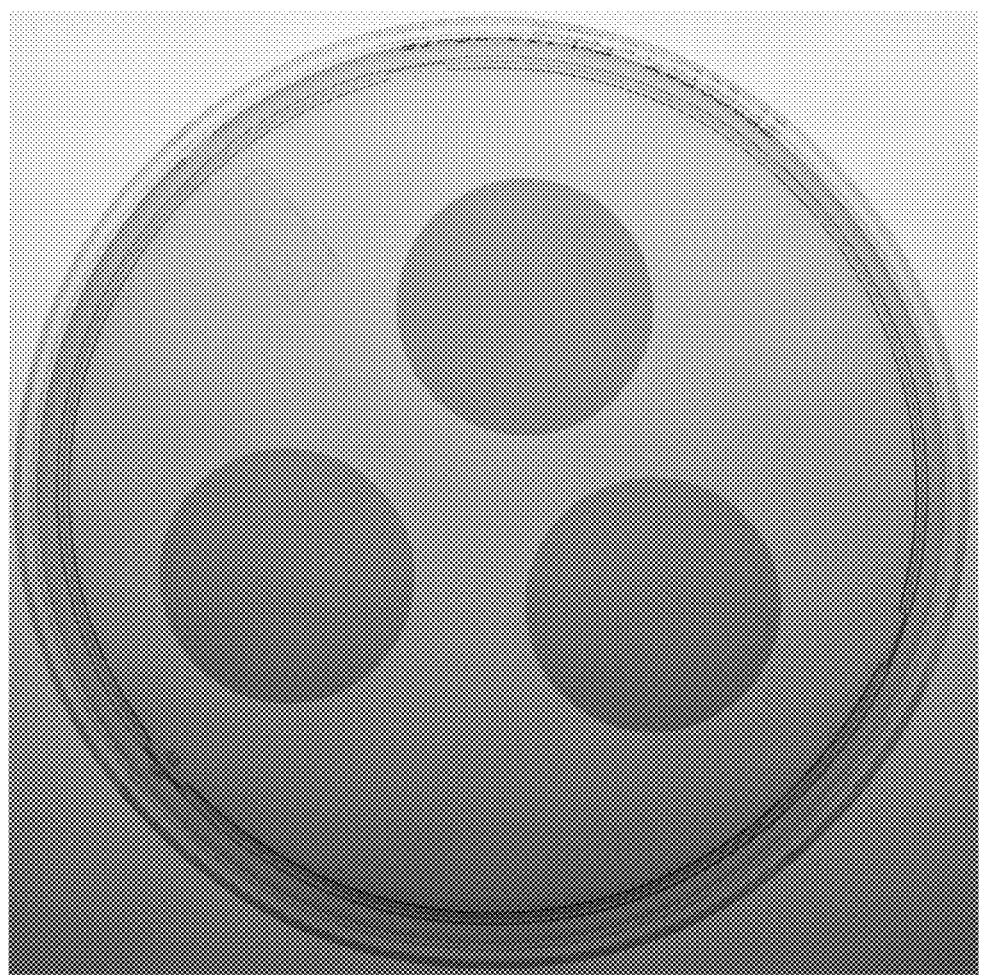

An aqueous solution of hydrogen peroxide with hydrogen peroxide concentration at 3% (w/v) was obtained (Walgreens, Allston, Mass.) and sprayed onto these bacteria-deposited membranes, followed by drying with a small blower and placing the membranes matte side up onto an agar plate. FIG. 14 shows these three membranes on the agar plate after overnight incubation at 37° C. No bacterial colonies are seen on these membranes indicating that all deposited bacteria were inactivated or killed.

A second set of membranes were prepared by depositing 150 µL of the 100,000-fold dilution of the as-received solution of Escherichia coli. Using the guidance from Example 4, it is estimated that 50 bacteria were deposited onto each of these membranes.

Figure 15:
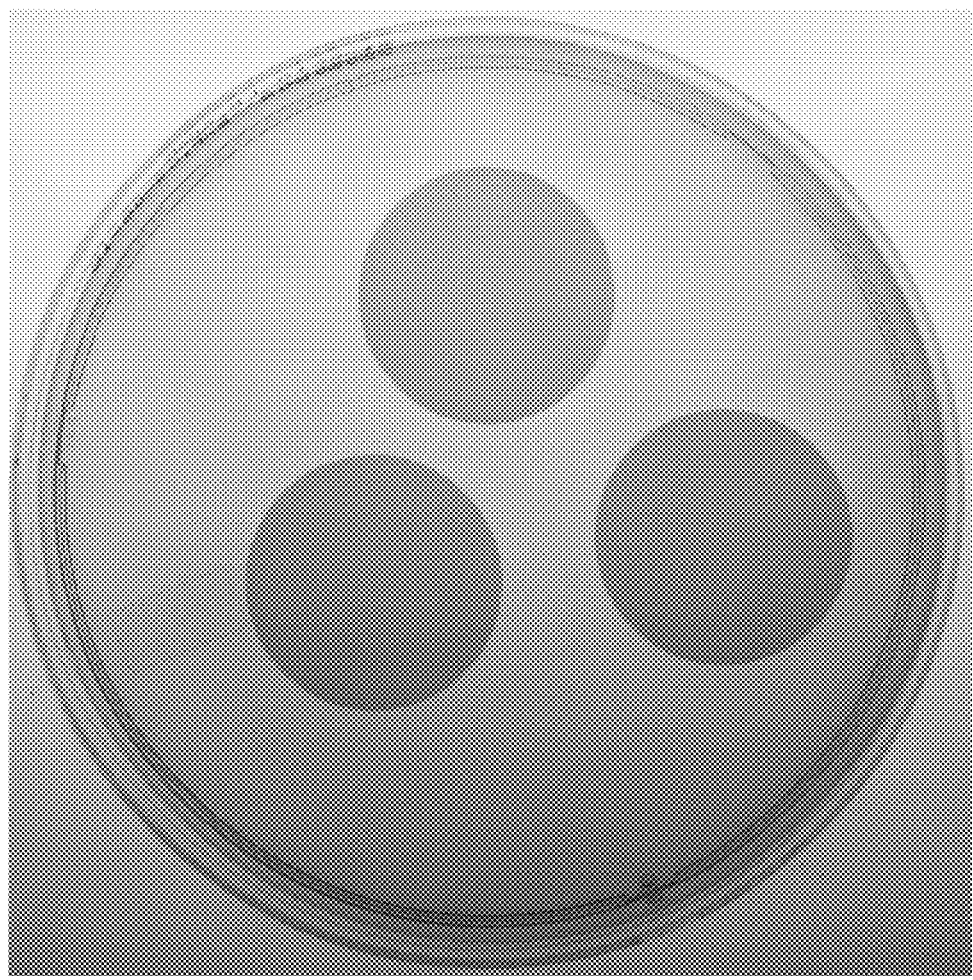

An aqueous solution of hydrogen peroxide with hydrogen peroxide concentration at 3% (w/v) was obtained (Walgreens, Allston, Mass.) and sprayed onto these bacteria-deposited membranes, followed by drying with a small blower and placing the membranes matte side up onto an agar plate. FIG. 15 shows these three membranes on the agar plate after overnight incubation at 37° C. No bacterial colonies are seen on these membranes indicating that all deposited bacteria were inactivated or killed.

A third set of membranes were prepared by depositing 150 µL of the 1,000,000-fold dilution of the as-received solution of Escherichia coli. Using the guidance from Example 4, it is estimated that 5 bacteria were deposited onto each of these membranes.

Figure 16:
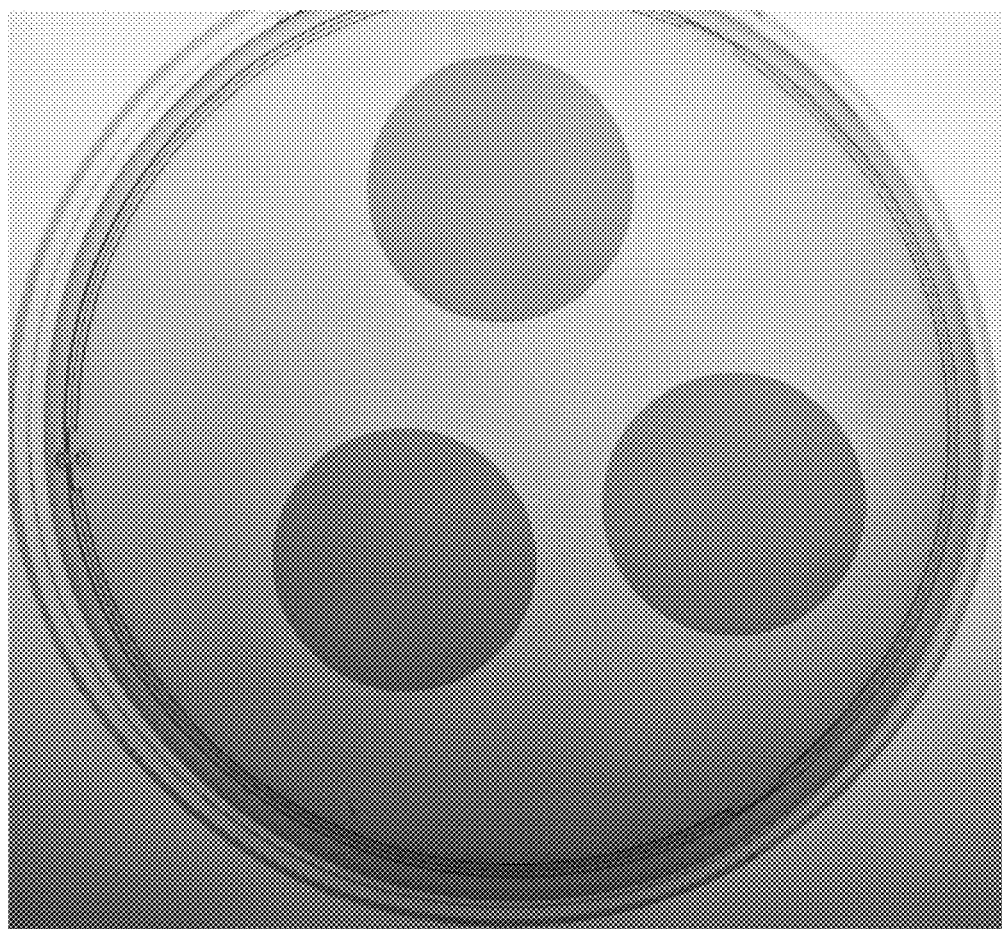

An aqueous solution of hydrogen peroxide with hydrogen peroxide concentration at 3% (w/v) was obtained (Walgreens, Allston, Mass.) and sprayed onto these bacteria-deposited membranes, followed by drying with a small blower and placing the membranes matte side up onto an agar plate. FIG. 16 shows these three membranes on the agar plate after overnight incubation at 37° C. No bacterial colonies are seen on these membranes indicating that all deposited bacteria were inactivated or killed.

Results from the first set of membranes in this example indicate the inactivation of approximately 500 bacteria on the membranes from this first set. This finding shows that a brief spraying with a dilute aqueous solution of hydrogen peroxide (3%), followed by rapid drying, can produce at least a 2.7 log reduction in the bacterial population on the treated surface.

Example 6

This example describes the inactivation of bacteria on polycarbonate membranes from a brief spray of a dilute aqueous solution of hydrogen peroxide (1% w/v and 0.33% w/v), followed by rapid drying. For these experiments, the deposition of bacteria onto polycarbonate membranes followed by spraying the hydrogen peroxide solution and drying the membrane with forced air, was performed using the materials, equipment and methods described in Example 4.

Membranes were prepared by depositing 150 µL of the 10,000-fold dilution of the as-received solution of Escherichia coli. Using the guidance from Example 4, it is estimated that 500 bacteria were deposited onto each of these membranes.

An aqueous solution of hydrogen peroxide with hydrogen peroxide concentration at 3% (w/v) was obtained (Walgreens, Allston, Mass.), diluted 3-fold and 3-fold again to give 1% (w/v) and 0.33% (w/v) aqueous solutions of hydrogen peroxide.

Figure 17:
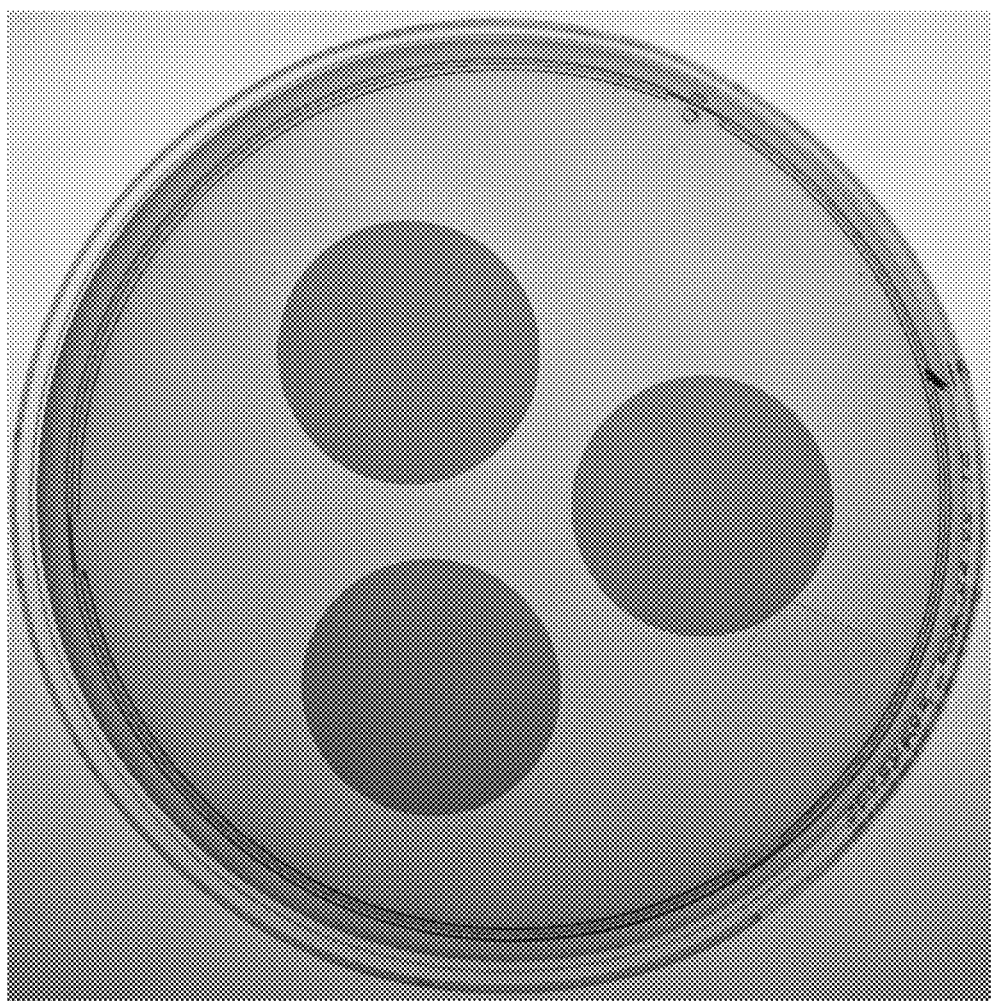

The 1% (w/v) aqueous solution of hydrogen peroxide was sprayed onto a first set of bacteria-deposited membranes, followed by drying with a small blower and placing the membranes matte side up onto an agar plate. FIG. 17 shows these three membranes on the agar plate after overnight incubation at 37° C. No bacterial colonies are seen on these membranes indicating that all deposited bacteria were inactivated or killed.

Figure 18:
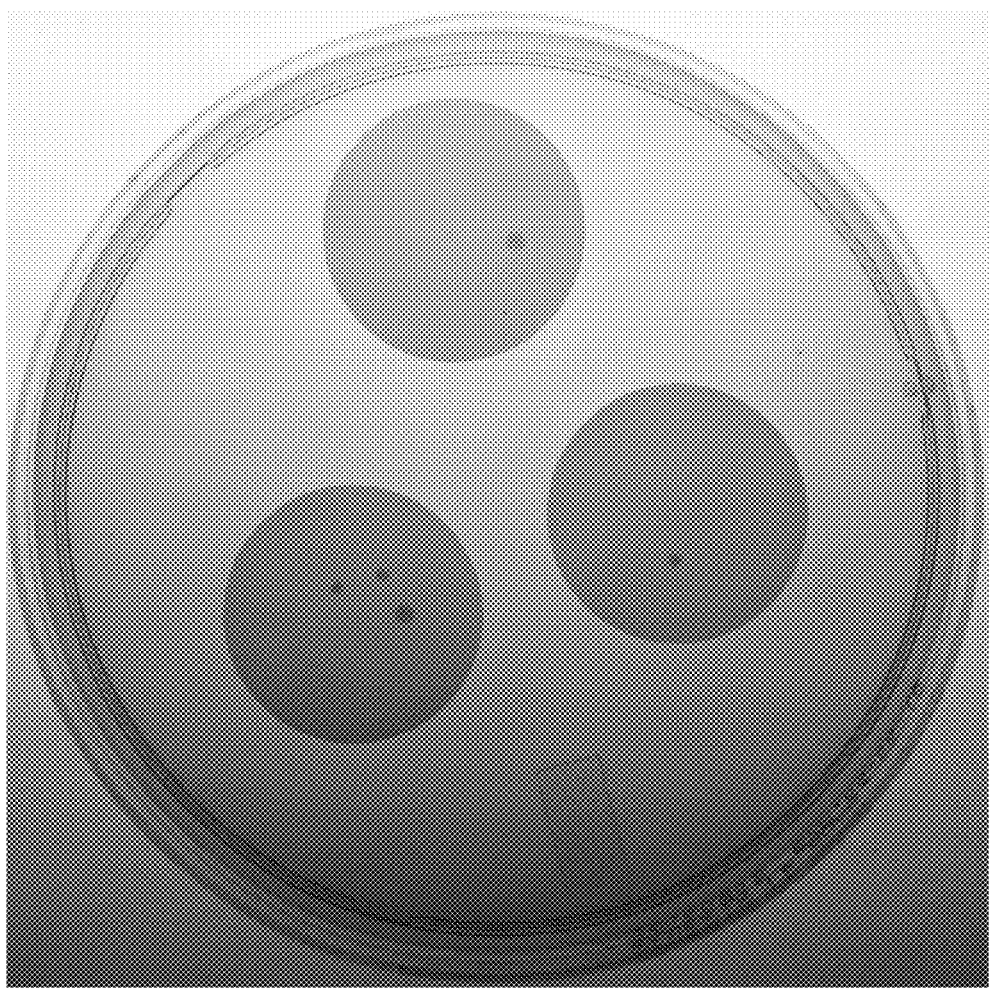

The 0.33% (w/v) aqueous solution of hydrogen peroxide was sprayed onto a second set of bacteria-deposited membranes, followed by drying with a small blower and placing the membranes matte side up onto an agar plate. FIG. 18 shows these three membranes on the agar plate after overnight incubation at 37° C. Three bacterial colonies are seen on one of the membranes while the remaining membranes each contain only one bacterial colony.

It can be noted that, while the reduction of hydrogen peroxide concentration from 3% (w/v) to 1% (w/v) to 0.33% (w/v) appears to reduce the efficacy of the pathogen inactivation or killing fluid, the 0.33% (w/v) hydrogen peroxide solution still retains substantial efficacy.

Example 7

This example describes the inactivation of bacteria on polycarbonate membranes from a brief spray of a dilute solution of hypochlorous acid, followed by rapid drying. For these experiments, the deposition of bacteria onto polycarbonate membranes followed by spraying the hypochlorous acid solution and drying the membrane with forced air, was performed using the materials, equipment and methods described in Example 4.

A first set of membranes were prepared by depositing 150 µL of the 10,000-fold dilution of the as-received solution of *Escherichia coli*. Using the guidance from Example 4, it is estimated that 500 bacteria were deposited onto each of these membranes.

Figure 19:
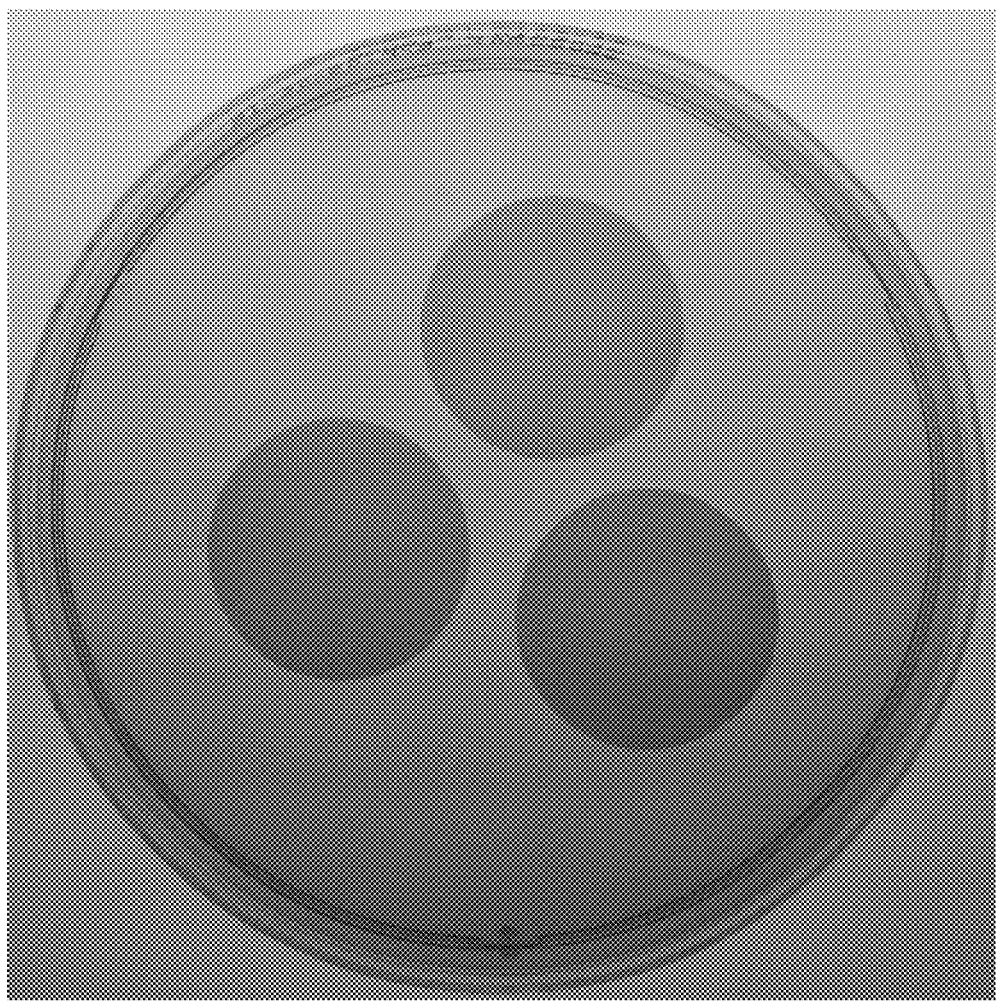

An aqueous solution of hypochlorous acid with hypochlorous acid concentration of 0.046% was obtained (Excelyte, Integrated Environmental Technologies, LTD., Little River, S.C.) and sprayed onto these bacteria-deposited membranes, followed by drying with a small blower and placing the membranes matte side up onto an agar plate. FIG. 19 shows these three membranes on the agar plate after overnight incubation at 37° C. No bacterial colonies are seen on these membranes indicating that all deposited bacteria were inactivated or killed.

A second set of membranes were prepared by depositing 150 µL of the 100,000-fold dilution of the as-received solution of *Escherichia coli*. Using the guidance from Example 4, it is estimated that 50 bacteria were deposited onto each of these membranes.

Figure 20:
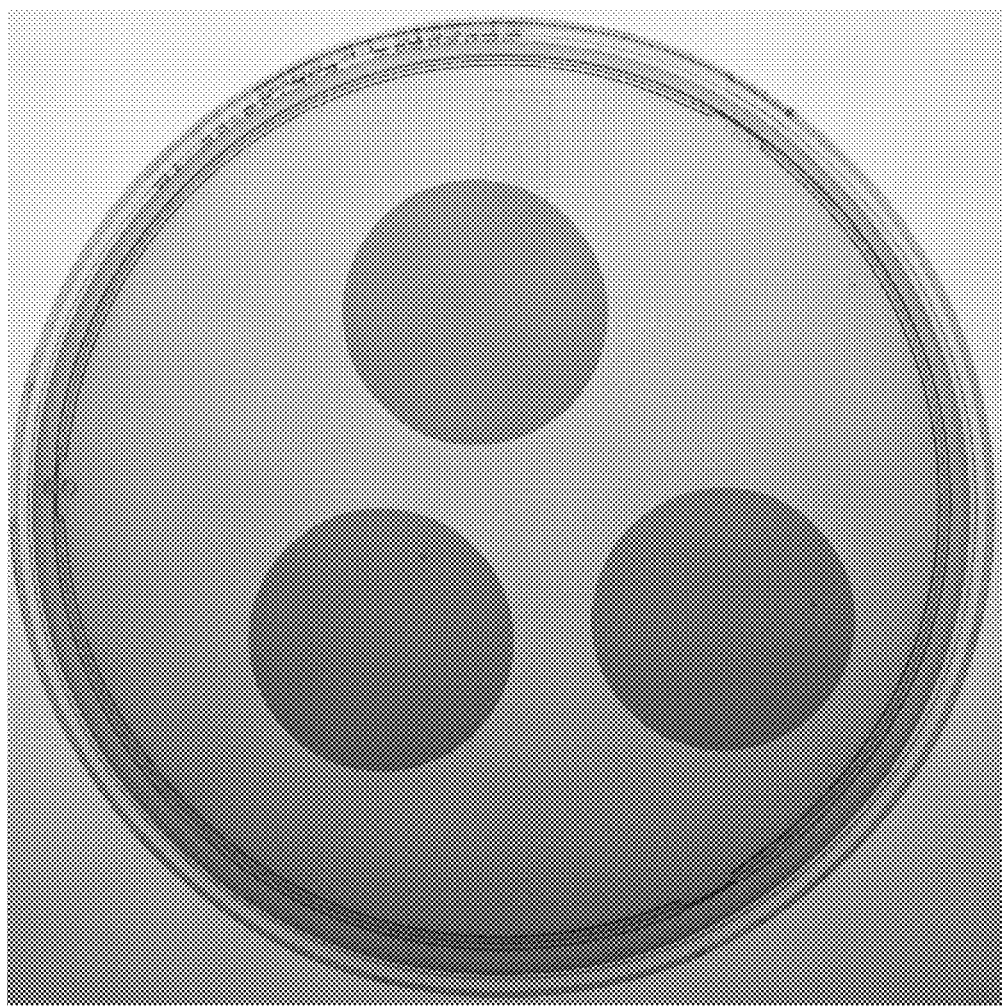

An aqueous solution of hypochlorous acid with hypochlorous acid concentration of 0.046% was obtained (Excelyte, Integrated Environmental Technologies, LTD., Little River, S.C.) and sprayed onto these bacteria-deposited membranes, followed by drying with a small blower and placing the membranes matte side up onto an agar plate. FIG. 20 shows these three membranes on the agar plate after overnight incubation at 37° C. No bacterial colonies are seen on the membrane at the top of the figure but there may be a single bacterial colony on the other two membranes shown in the figure.

A third set of membranes were prepared by depositing 150 µL of the 1,000,000-fold dilution of the as-received solution of *Escherichia coli*. Using the guidance from Example 4, it is estimated that 5 bacteria were deposited onto each of these membranes.

Figure 21:
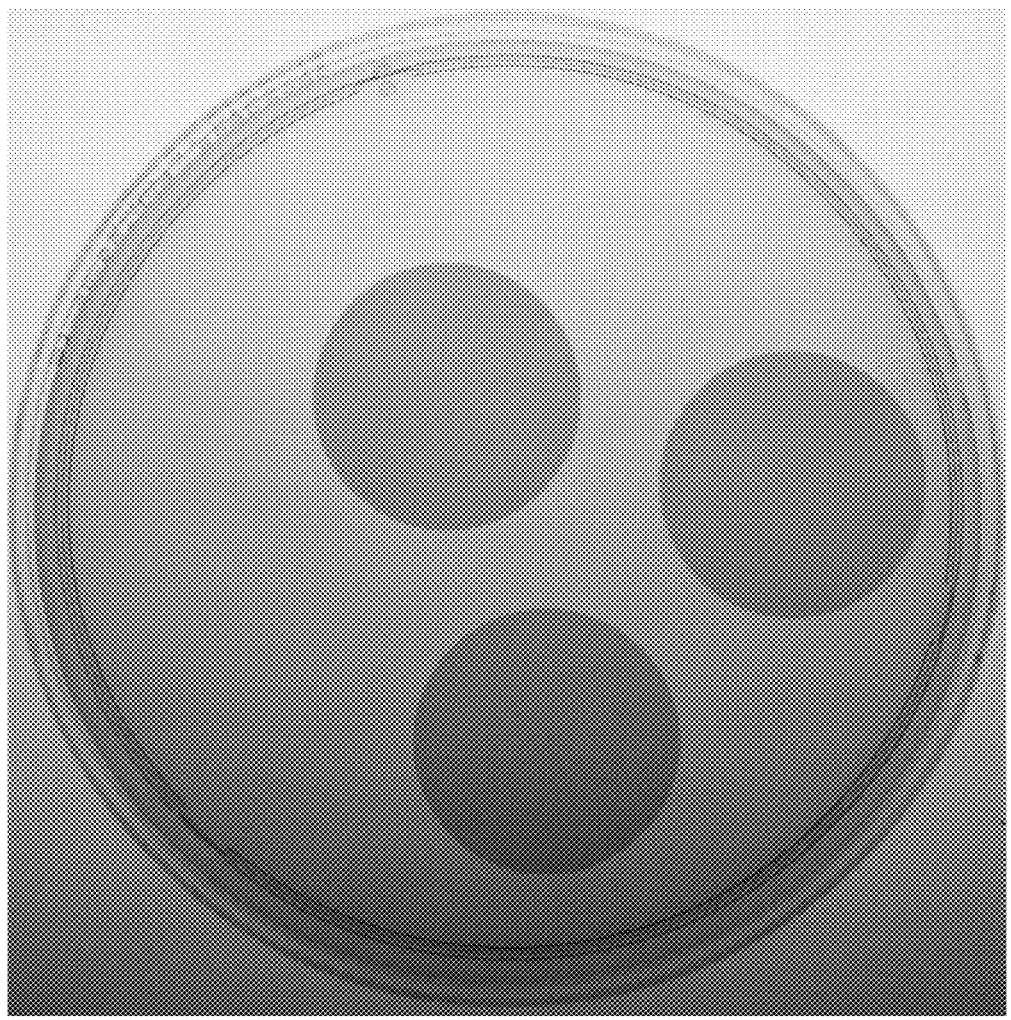

An aqueous solution of hypochlorous acid with hypochlorous acid concentration of 0.046% was obtained (Excelyte, Integrated Environmental Technologies, LTD., Little River, S.C.) and sprayed onto these bacteria-deposited membranes, followed by drying with a small blower and placing the membranes matte side up onto an agar plate. FIG. 21 shows these three membranes on the agar plate after overnight incubation at 37° C. No bacterial colonies are seen on these membranes indicating that all deposited bacteria were inactivated.

Results from the first set of membranes in this example indicate the inactivation of approximately 500 bacteria on the membranes from this first set. This finding shows that a brief spray of a dilute aqueous solution of hypochlorous acid, followed by rapid drying, can produce at least a 2.7 log reduction in the bacterial population on the treated surface.

Example 8

This example describes the inactivation of bacteria on polycarbonate membranes from a brief spray of an aqueous solution of isopropyl alcohol, followed by rapid drying. For these experiments, the deposition of bacteria onto polycarbonate membranes followed by spraying the hypochlorous acid solution and drying the membrane with forced air, was performed using the materials, equipment and methods described in Example 4.

A first set of membranes were prepared by depositing 150 µL of the 10,000-fold dilution of the as-received solution of *Escherichia coli*. Using the guidance from Example 4, it is estimated that 500 bacteria were deposited onto each of these membranes.

Figure 22:
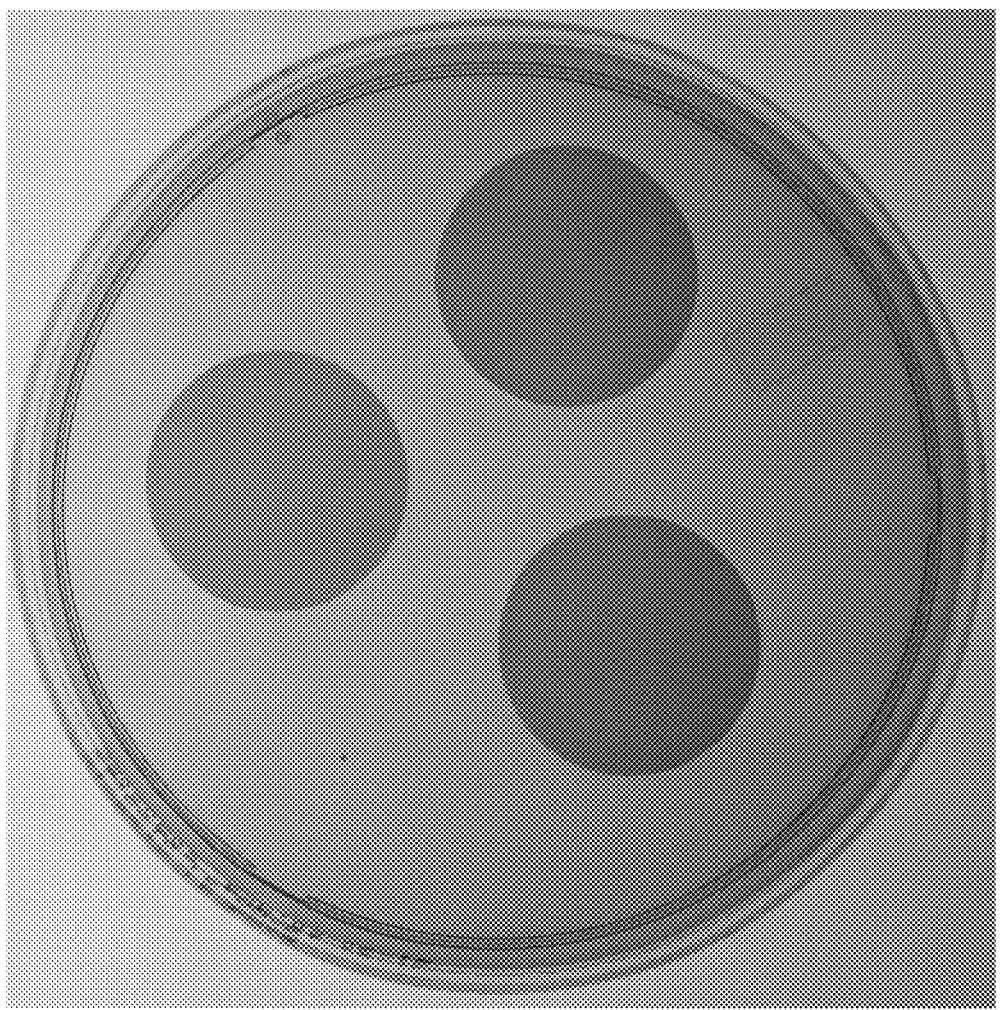

An aqueous solution of isopropyl alcohol with isopropyl alcohol concentration of 70% was obtained (CVS, Belmont, Mass.) and sprayed onto these bacteria-deposited membranes, followed by drying with a small blower and placing the membranes matte side up onto an agar plate. FIG. 22 shows these three membranes on the agar plate after overnight incubation at 37° C. No bacterial colonies are seen on these membranes indicating that all deposited bacteria were inactivated or killed.

A second set of membranes were prepared by depositing 150 µL of the 100,000-fold dilution of the as-received solution of *Escherichia coli*. Using the guidance from Example 4, it is estimated that 50 bacteria were deposited onto each of these membranes.

An aqueous solution of isopropyl alcohol with isopropyl alcohol concentration of 70% was obtained (CVS, Belmont, Mass.) and sprayed onto these bacteria-deposited membranes, followed by drying with a small blower and placing the membranes matte side up onto an agar plate. FIG. 23 shows these three membranes on the agar plate after overnight incubation at 37° C. No bacterial colonies are seen on these membranes indicating that all deposited bacteria were inactivated or killed.

A third set of membranes were prepared by depositing 150 µL of the 1,000,000-fold dilution of the as-received solution of *Escherichia coli*. Using the guidance from Example 4, it is estimated that 5 bacteria were deposited onto each of these membranes.

An aqueous solution of isopropyl alcohol with isopropyl alcohol concentration of 70% was obtained (CVS, Belmont, Mass.) and sprayed onto these bacteria-deposited membranes, followed by drying with a small blower and placing the membranes matte side up onto an agar plate. FIG. 24 shows these three membranes on the agar plate after overnight incubation at 37° C. No bacterial colonies are seen on these membranes indicating that all deposited bacteria were inactivated or killed.

Results from the first set of membranes in this example indicate the inactivation of approximately 500 bacteria on the membranes from this first set. This finding shows that a brief spray of an aqueous solution of isopropyl alcohol, followed by rapid drying, can produce at least a 2.7 log reduction in the bacterial population on the treated surface.

Example 9

This example describes inactivation of bacterial spores on polycarbonate membranes from a brief spray of an aqueous solution of hydrogen peroxide, followed by rapid drying. The aqueous solutions of hydrogen peroxide used in this example were diluted using distilled water or used as-received from an aqueous (12%) hydrogen peroxide solution (O-W & Company, Fort Collins, Colo.). The airbrush used for the spraying of fluid is described in Example 1, along with the blower used for drying the membranes.

A solution of the 6633 cell line of *Bacillus subtilis* spores was obtained (NAMSA, Northwood, Ohio) and diluted 100-fold with distilled water to make a dilute spore solution containing approximately 190,000 spores per ml. Three track-etched polycarbonate membranes (Whatman Nucleopore, Sigma-Aldrich, St. Louis, Mo.), each 25 mm in diameter with 0.4 µm pores, were placed on a vacuum manifold (Millipore, Bedford, Mass.). With the vacuum draw operating, 150 µL of the diluted spore solution was pipetted onto the center of the exposed (matte) surface of each of the polycarbonate membranes. The solution was quickly pulled through the track-etched membrane, leaving approximately 30,000 spore on the exposed (matte) surface of each of the membranes. After 3 minutes of drying on the vacuum manifold, the membranes were further dried by holding each of the membranes under the airflow from a small blower.

These spore-deposited membranes were then placed on the surface of pre-cleaned laboratory bench and, using an airbrush, were sprayed with either distilled water, or an aqueous solution of 3%, 6%, 9% or 12% hydrogen peroxide for approximately 1 second and then dried for approximately 5 seconds by holding the membrane near the output of the small blower. It is estimated that the spray action has delivered a uniform coating, based on the observed reflective sheen on top of each membrane after each spray. After 5 seconds of drying from the small blower, the membranes appeared to be cleared of all fluid and fully dried and they were then placed onto an agar plate and allowed to incubate overnight at 37° C. The agar plates used for this example were pre-cast Luria broth (LB) agar plates (Carolina Biological Supply Company, Burlington, N.C.).

FIGS. 25A-25E show images of various spore-deposited and fluid-sprayed membranes on agar, after overnight incubation at 37° C. FIGS. 25A-25E are described in the reverse order herein. As shown in a panel 2501 in FIG. 25E, the images show substantial bacterial growth on the spore-deposited membranes that had received a brief spray of distilled water. Here, evidence for substantial bacterial growth is the (approximately) circular, dark patch at the center of each of the circular membranes. In the panel 2501, the dark patches include complete lawns of bacteria, grown up where the spore solution had been deposited onto the membranes and incubated overnight at 37° C., after water spraying and drying.

Figure 25A:
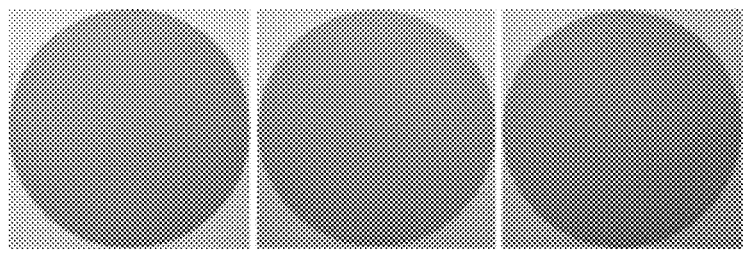
Figure 25B:
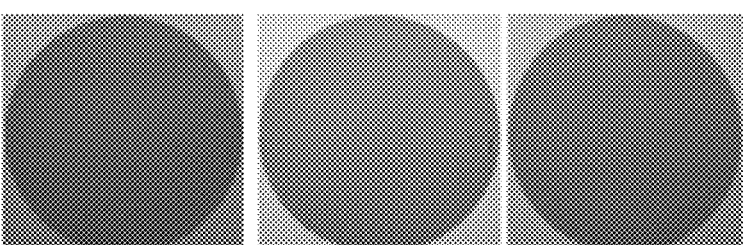
Figure 25C:
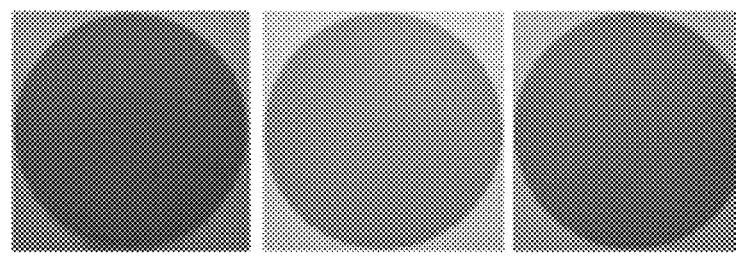
Figure 25D:
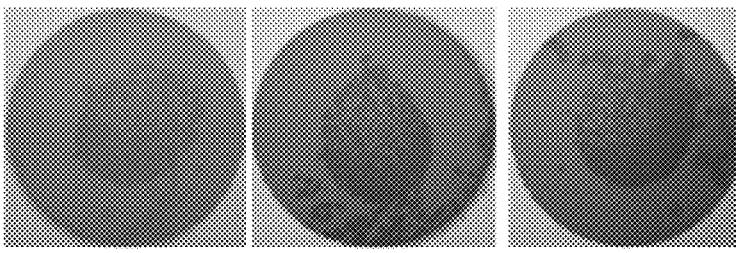
Figure 25E:
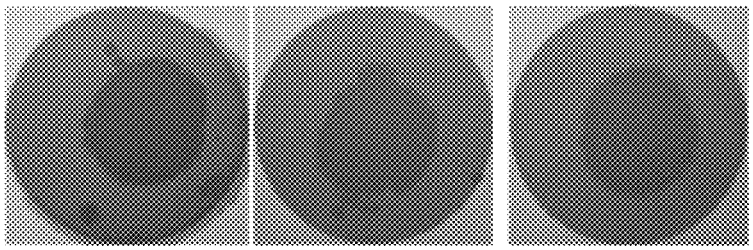

FIG. 25D (panel 2502) shows images demonstrating substantial bacterial growth on the spore-deposited membranes that had received a brief spray of an aqueous solution of 3% hydrogen peroxide. Here, evidence for substantial bacterial growth is the (approximately) circular, dark patch at the center of each of the circular membranes. In FIG. 25D, the dark patches include (nearly) complete lawns of bacteria grown up after overnight incubation at 37° C. where the spore solution had been deposited. Some evidence for the ability of an aqueous 3% hydrogen peroxide solution to quickly inactivate *Bacillus subtilis* spores may be seen through the appearance of small yet distinct dark patches within the larger dark patch at the center of each circular membrane. It is likely that these small, distinct patches correspond to isolated colonies that have grown up from spores that were not inactivated by the brief spray of an aqueous solution of 3% (w/v) hydrogen peroxide. The evidence for some degree of inactivation is seen from the appearance of regions that are clear or free of bacteria between these small yet distinct dark patches.

FIG. 25C (panel 2503) shows no bacterial growth on spore-deposited membranes that had received a brief spray of an aqueous solution of 6% (w/v) hydrogen peroxide. FIG. 25B (panel 2504) shows no bacterial growth on spore-deposited membranes that received a brief spray of an aqueous solution of 9% (w/v) hydrogen peroxide. Finally, FIG. 25A (panel 2505) shows no bacterial growth on spore-deposited membranes that had received a brief spray of an aqueous solution of 12% (w/v) hydrogen peroxide. In panels 2503 (FIG. 25C), 2504 (FIG. 25B) and 2505 (FIG. 25A), evidence for no bacterial growth, and therefore complete inactivation of the bacterial spores, is shown through the absence of dark patches, either small and distinct or large and complete, at the centers of each of the membranes where the spore solution had been deposited, prior to the spray of aqueous hydrogen peroxide solution, drying and subsequent overnight incubation at 37° C. In FIGS. 25A-25E, all of the membranes were imaged while situated on top of the agar media. This configuration allows for spores that have not been inactivated to germinate and proliferate and draw nutrients from the agar via the submicron diameter throughholes or pores within each membrane.

Notably, bacterial growth is not seen on the spore-deposited membranes that had been sprayed with aqueous solutions of 6%, 9% or 12% (w/v) hydrogen peroxide. The experiments, results of which are shown in FIGS. 25A-25E, establish that bacterial spores on surfaces can be inactivated with a brief spray of an aqueous solution of hydrogen peroxide, followed by rapid drying.

While the present disclosure has been described in conjunction with various embodiments and examples, it is not intended that the described techniques be limited to such embodiments or examples. On the contrary, the described techniques encompass various alternatives, modifications, and equivalents, as will be appreciated by those of skill in the art. Accordingly, the foregoing description and drawings are by way of example only.

What is claimed is:

1. A system for killing or inactivating a pathogen, comprising:
   a housing having
      a hand-receiving zone configured to receive at least one hand and having at least two nozzles, and
      an active agent receptacle in fluid communication with the at least two nozzles; and
   a control module configured to control the delivery of an active agent as an aerosol from the at least two nozzles in a delivery dose,
   wherein the control module is programmed to deliver the delivery dose to a target hand surface as a thin, dried coating in a time period that is less than or equal to 10 seconds.

2. The system of claim 1, further comprising an air tank configured to provide air to the at least two nozzles.

3. The system of claim 1, further comprising a pressure regulator configured to control pressure at the at least two nozzles.

4. The system of claim 1, further comprising a display communicatively coupled to the control module and configured to display information related to operation of the system.

5. The system of claim 4, wherein the display comprises an interactive display configured to receive instructions related to operation of the system.

6. The system of claim 1, further comprising at least one sensor configured to detect presence of the target hand surface in proximity to the at least two nozzles.

7. The system of claim 1, further comprising a drying component configured to dry the delivery dose delivered to the target hand surface.

8. The system of claim 1, wherein the active agent receptacle houses a removable and refillable reagent-containing cartridge.

9. The system of claim 1, wherein the active agent receptacle is configured as a reservoir that receives a supply of the active agent.

10. The system of claim 1, wherein the active agent comprises a solution selected from the group consisting of an aqueous solution of hydrogen peroxide, an aqueous solution of hypochlorous acid, an aqueous solution of isopropyl alcohol, an aqueous solution of ethanol, an aqueous solution of peracetic acid, an aqueous solution of acetic acid, an aqueous solution of sodium hypochlorite, an aqueous solution of ozone, and any combination thereof.

11. The system of claim 10, wherein the aqueous solution of hydrogen peroxide comprises from about 0.3% to about 15% of hydrogen peroxide.

12. The system of claim 11, wherein the aqueous solution of hydrogen peroxide comprises about 0.33%, 1%, 3%, 6%, 9%, or 12% of hydrogen peroxide.

13. The system of claim 10, wherein the aqueous solution of hypochlorous acid comprises at least about 0.046% of hypochlorous acid.

14. The system of claim 10, wherein the aqueous solution of isopropyl alcohol comprises at least about 70% of isopropyl alcohol.

15. The system of claim 1, wherein the active agent comprises an aqueous mixture of peracetic acid and hydrogen peroxide.

16. The system of claim 1, wherein one of the at least two nozzles is a stationary nozzle.

17. The system of claim 1, wherein the at least two nozzles comprise two or more stationary nozzles.

18. The system of claim 1, wherein the at least two nozzles comprise two or more moveable nozzles.

19. The system of claim 1, further comprising at least one actuator configured to receive user input to activate the at least two nozzles.

20. The system of claim 1, wherein the at least two nozzles are configured to deliver a layer of the active agent to the target hand surface, the layer having a thickness from about 1 µm to about 50 µm.

21. The system of claim 20, wherein the layer has a thickness from about 5 µm to about 20 µm.

22. The system of claim 1, wherein the at least two nozzles are ultrasonic nozzles.

23. The system of claim 1, wherein the at least two nozzles comprise airflow-based atomizing nozzles.

24. The system of claim 1, wherein the at least two nozzles comprise pressure-based fluid nozzles.

25. The system of claim 1, wherein the system is mountable to a support.

26. The system of claim 1, wherein the hand-receiving zone has a configuration that conforms to a shape of one or two hands.

27. The system of claim 1, wherein the hand-receiving zone comprises an enclosure, and wherein the at least two nozzles are arranged such that orifices of the at least two nozzles are disposed along inner walls of the enclosure.

28. The system of claim 1, wherein the at least two nozzles are disposed at opposed sides of the hand-receiving zone.

29. The system of claim 1, wherein the control module is programmed to deliver the delivery dose to the target hand surface as a thin, dried coating in a time period that is less than or equal to 5 seconds.

30. The system of claim 10, wherein the aqueous solution of isopropyl alcohol comprises at least about 60% of isopropyl alcohol.

31. The system of claim 10, wherein the aqueous solution of hypochlorous acid comprises from about 0.005% to about 1% of hypochlorous acid.

* * * * *